United States Patent
Shirai et al.

(10) Patent No.: US 7,439,522 B2
(45) Date of Patent: Oct. 21, 2008

(54) COUNTING SYSTEM FOR FLUORESCENT MOLECULES

(75) Inventors: Masataka Shirai, Higashimurayama (JP); Tsuyoshi Sonehara, Kokubunji (JP); Takashi Anazawa, Koganei (JP); Chifumi Gouda, Kokubunji (JP); Chihiro Uematsu, Kawasaki (JP)

(73) Assignee: Hitachi High-Technologies Corporation, Tokyo (JP)

(*) Notice: Subject to any disclaimer, the term of this patent is extended or adjusted under 35 U.S.C. 154(b) by 113 days.

(21) Appl. No.: 11/349,898

(22) Filed: Feb. 9, 2006

(65) Prior Publication Data

US 2006/0197034 A1   Sep. 7, 2006

(30) Foreign Application Priority Data

Mar. 4, 2005 (JP) ............... 2005-059858
Oct. 19, 2005 (JP) ............... 2005-303835

(51) Int. Cl.
*G01N 21/64* (2006.01)
(52) U.S. Cl. ................ 250/458.1; 250/459.1
(58) Field of Classification Search ........... 250/458.1, 250/459.1
See application file for complete search history.

(56) References Cited

U.S. PATENT DOCUMENTS

| 5,296,911 | A  | * | 3/1994  | Weyrauch et al. ............. 356/73 |
| 5,366,608 | A  | * | 11/1994 | Kambara ....................... 204/603 |
| 6,999,173 | B2 | * | 2/2006  | Kleinfeld et al. ............. 356/417 |
| 7,186,988 | B2 | * | 3/2007  | Muller et al. .............. 250/458.1 |
| 2003/0095254 | A1 | * | 5/2003 | Tanaami ....................... 356/317 |
| 2003/0178577 | A1 | * | 9/2003 | Aronkyto ................... 250/458.1 |
| 2004/0178357 | A1 | * | 9/2004 | King ......................... 250/458.1 |
| 2005/0068534 | A1 | * | 3/2005 | Kleinfeld et al. ............ 356/417 |
| 2006/0152727 | A1 | * | 7/2006 | Bickmore et al. ........... 356/417 |
| 2007/0008536 | A1 | * | 1/2007 | Mitani et al. ................ 356/417 |

FOREIGN PATENT DOCUMENTS

| JP | 63-021556 | 1/1988 |
| JP | 07-134101 | 5/1995 |
| JP | 08-105834 | 4/1996 |
| JP | 09-043197 | 2/1997 |

(Continued)

OTHER PUBLICATIONS

Electophoretic Quantitiation of Nucleic Acids without Amplification by Single-Molecule Imaging; Oct. 1, 2002; vol. 74, No. 19; Analytical Chemistry; United States.

*Primary Examiner*—David P. Porta
*Assistant Examiner*—Mark R Gaworecki
(74) *Attorney, Agent, or Firm*—Antonelli, Terry, Stout & Kraus, LLP.

(57) ABSTRACT

Single molecule measurement is conducted by propagating a laser light under multiple reflection between two substrates constituting a flow channel for flowing a sample solution, exciting target molecules in the sample, detecting one-dimensional images of generated fluorescence by a one-dimensional detection portion, synthesizing two-dimensional images from the obtained one-dimensional images by a data synthesizing portion and measuring the concentration of target molecules in the sample solution by counting the number of target molecules based on the two-dimensional images, thereby measuring the concentration of the target molecules in the sample solution. These constitutions for single molecule measurement lead to high precision determination of a micro-amount of a biological material.

28 Claims, 18 Drawing Sheets

FOREIGN PATENT DOCUMENTS

| | | |
|---|---|---|
| JP | 09-210910 | 8/1997 |
| JP | 09-229859 | 9/1997 |
| JP | 2003-177097 | 6/2003 |
| WO | WO 96/24042 | 8/1996 |
| WO | WO 96/24043 | 8/1996 |
| WO | WO 00/25113 | 10/1999 |

* cited by examiner

COUNTING SYSTEM FOR FLUORESCENT MOLECULES

CLAIM OF PRIORITY

The present application claims priority from Japanese applications JP 2005-059858 filed on Mar. 4, 2005, JP-2005-303835 filed on Oct. 19, 2005, the contents of which are hereby incorporated by reference into this application

FIELD OF THE INVENTION

The present invention concerns a counter or an in vitro clinical test equipment for quantitative determination of a micro-amount of a biological material such as DNA (deoxypentose nucleic acid) or RNA (ribonucleic acid), or protein sampled from a biological body not by way of a process of chemical amplification. Particularly, it relates to a counter or in vitro clinical test equipment based on the principle of measurement of specifically fluorescence-labeling a biological material intended for quantitative determination and conducting laser-induced fluorescence measurement by laser excitation.

BACKGROUND OF THE INVENTION

For quantitative determination of a micro-amount of biological material such as DNA, chemical amplification such as a PCR (Polymerase Chain Reaction) method is generally utilized. In the utilization of the chemical amplification method, the amount of the biological material is estimated by quantitative determination of products after the amplification. However, since amplification efficiency always fluctuates, estimation in the quantitative determination for the biological material is inacurate. In order to solve the problem, it has been desired for direct quantitative determination of the micro-amount of the biological material without using the chemical amplification. One of the methods of attaining the same is a method referred to as single molecule counting.

The single molecule counting means a method of bonding a fluorescence-label with a biological material of an object for the quantitative determination and counting fluorescence-labeled molecules by laser excitation (for example, refer to "Analytical Chemistry", vol. 74, No. 19 (2002), p. 5033). "Analytical Chemistry", vol. 74, No. 19 (2002), p. 5033 describes that DNA molecules by the number of about 1,000 in 0.3 µL of a sample solution can be detected. FIG. 1 shows a constitutional view of a detection system for practicing the existent method. A laser light for exciting fluorescence-labeled molecules is emitted from a laser light source 1, passed through a shutter 2 for adjusting an exposure time, focused through a lens 3 and then inputted to a capillary 12. A sample solution containing a biological material intended for quantitative determination (hereinafter referred to as a target) is filled in the capillary. The target molecule is fluorescence-labeled before introduction into the capillary 12. Accordingly, in a case where the target molecule is contained in the sample solution, fluorescence is emitted by a light incident to the capillary. In this case, the target molecule is dispersed in the sample solution, and the target molecule in an irradiated region with the laser (volume: $5 \times 10^{-11}$ L) in the capillary appears as a minute luminous body. For detecting such a minute luminous body, images of the laser irradiation region is focused by an objective lens 6 on a CCD (Charge Coupled Device) 8 in a camera 7 to obtain fluorescent images. In the acquired image data, the luminous body is distinguished from the background in the laser irradiation region and the number thereof is counted to conduct quantitative determination of concentration of the target molecules.

Then, FIG. 2 shows an enlarged view for a region in the capillary to be irradiated with a laser. A laser light 13 the spot of which is shaped into an elliptic shape by two cylindrical lenses is irradiated to a capillary 12 filled with the sample solution and having a square cross section. The fluorescence-labeled target molecule 14 is electrophoretically moved by 90 µm/sec in the direction 15.

As can be seen from FIG. 1 and FIG. 2, an electrophoretic direction 15 and an incident direction 5 of a laser light are perpendicular to each other. This is a constitution necessary for measuring the concentration of the electrophoretically moved target molecule on every moving distance. Such a constitution is also described in JP-A Nos. 21556/1988, 134101/1995, 105834/1996, 43197/1997, and 210910/1997. Further, in the existent examples described above, gel is inserted between the two sheets of glass substrates and molecules in the gel are separated on every molecular size due to the electrophoresis of the molecules in the gel. Target molecules on every molecular size are excited by a laser beam passing between the two sheets of glass substrates to quantitatively determine the concentration on every molecular size by measurement of fluorescent intensity.

Further, in the method disclosed in the "Analytical Chemistry", vol. 74, No. 19 (2002), p. 5033 and in JP-A Nos. 21556/1988, 134101/1995, 105834/1996, 43197/1997, and 210910/1997, the measuring direction by fluorescence and the incident direction of the laser light are set perpendicular to each other. Further, JP-A No. 229859/1995, JP-W Nos. 513555/1998, and 513556/1998 disclose a constitution in which the direction of the laser excitation and the measuring direction of fluorescence are perpendicular to each other although not using the electrophoresis. Particularly, in JP-A No. 229859/1997, a fluorescence material or a sample containing a fluorescence material intended for fluorescence measurement is filled in the sample container and the laser light is incident from one end of the sample container, passed in the inside and then emitted at the other end. The sample container has a shape elongated along the propagating direction of the laser light and formed of a transparent material such as glass. It is described that the accumulated value of the fluorescence intensity is detected in the direction substantially perpendicular to the pulse excited light based on the signal in synchronization with the output timing of the pulse excited light by using this constitution, to calculate the fluorescence life. Further, JP-A Nos. 513555/1988 and 513556/1998 also describe that a gel is filled between two sheets of glass plates and a laser light is incident from the end of the glass plate to the inside of the gel. The concentration of fluorescence present in the gel is measured with this constitution.

Further, JP-A No. 177097/2003 (Patent Document 10) discloses a constitution in which a laser light is entered in a chip for optical measurement and the direction of the fluorescence measurement and the direction of the incident laser light are made different.

On the other hand, JP-A No. 528714/2002 discloses that a sample solution containing a target is held on a plane and excited by a laser light from the rear face or the upper surface of the sample solution to detect fluorescence from the fluorescence-labeled target molecules. Particularly, it is described that the sample can be scanned (moved) to a detector for quantitative determination of target concentration in many sample solutions by fluorescence measurement in this system.

SUMMARY OF THE INVENTION

In the constitution disclosed in the "Analytical Chemistry", vol. 74, No. 19 (2002), p. 5033, the measurement volume in the sample solution is extended to more than a laser irradiation volume by the movement of a target 14 also in a state where the laser light 13 is fixed. However, since this accompanies electrophoresis, it requires much time for extending the volume that can be measured. For example, in the "Analytical Chemistry", vol. 74, No. 19 (2002), p. 5033, the volume that can be measured is only 0.29 µL in 10 min. Generally, in the application use of medical and biological measurement, it is desirable that several tens µL of volume can be measured. At first, the measuring system in the "Analytical Chemistry", vol. 74, No. 19 (2002), p. 5033 is to be described. In this known example, as shown in FIG. 1, fluorescence from the fluorescence-labeled target molecule 14 in the capillary 12 is measured by a CCD (Charge Coupled Device) 8. Relevant matters to the measuring time are to be described more specifically. A synchronization signal is sent by way of a signal line 10 to a shutter 2 and a CCD 8 as shown in FIG. 1 to properly synchronize the exposure time and a time of frame. The time of frame indicates a time of one cycle from photographing for one frame to photographing for the succeeding frame, and the exposure time indicates a time in which a laser is irradiated into the sample solution within the one frame time. Fluorescence images emitted during the exposure time in which the laser is irradiated is converted by the CCD 8 into electrical signals and put to image processing to complete photographing. For shortening the measuring time, the time of frame has to be shortened. On the other hand, the time of frame is defined by the width of a laser irradiation region and the electrophoretic speed of a molecule. When the target molecule 14 has completed traversing over the width 17 of the laser irradiation region in FIG. 2 by electrophoresis, photographing for the next frame can be started. That is, the time of frame is in an inverse proportion with the electrophoretic speed, and in proportion with the irradiation region width 17. For extending the measurement volume, it is necessary to either increase the electrophoretic speed thereby shortening the time of frame, or extend the laser irradiation volume 16, that is, a volume of sample solution that can be measured at a time.

However, the time of frame can not be shortened greatly by the reasons described below. At first, in a case where the electrophoretic speed is increased to shorten the time of frame, since the fluorescence-labeled target appeared dotwise in a state where the exposure time was maintained flows and appears as a rod-like shape to lower the fluorescence intensity per 1 pixel that can be measured, measurement is no more possible. Further, in a case of shortening the exposure time thereby shortening the time of frame, the amount of fluorescence that can be taken into the CCD 8 is decreased and no clear photographing is possible. In this case, while the intensity of the excitation laser may be increased in order to prevent lowering of the amount of the fluorescence, the intensity is restricted in a small-sized laser light source available at a sufficiently reduced cost. Accordingly, the time of frame can not be shortened greatly.

Further, in a case of increasing the irradiation volume, that is, the width 17 or the height 18 of the focused laser beam for increasing the volume of the sample solution that can be measured at a time, it lowers the laser excitation density, and images can not be obtained under the condition where the exposure time is constant. Further, in a case of extending a width 19 of the capillary, this inevitably increases a capillary height 20 with the reason in view of manufacture. In this case, the region in the capillary not irradiated with the laser is extended in proportion with the difference between the capillary height 20 and the laser spot height 18. Since this means increase of the not measured volume, this results in an error in a case of quantitative determination of a sample containing only a micro-amount of target.

Further, it is considered for a case of labeling various kinds of fluorescence-labeled target molecules in a sample solution with phosphors that are different from each other and conducting fluorescent measurement while distinguishing emission wavelengths different from each other with an aim of conducting simultaneous quantitative determination for various kinds of the target molecules. In this case, in the method disclosed in the "Analytical Chemistry", vol. 74, No. 19 (2002), p. 5033, since the electrophoretic speed differs depending on the targets, the optimal time of frame is different depending on the target. Accordingly, since the time of frame has to be decided conforming to the target at a slow electrophoretic speed, it gives rise to a problem of resulting in increase of the measuring time.

In the constitution of moving fluorescence-labeled target molecules by electrophoresis in the sample, since the sample solution is introduced into a container inserted with electrodes, it needs a great amount of the sample solution. Further, since the entire sample solution can not be measured, accurate quantitative determination is difficult in a case where the target molecules are contained only by an extremely small number (for example, about 50 molecules) in the sample solution. Further, in a case of measuring a number of target molecules simultaneously while labeling them by different phosphors, it gives rise to a problem in view of measurement due to the difference of electrophoresis speed.

While the electrophoresis is utilized in the "Analytical Chemistry", vol. 74, No. 19 (2002), p. 5033 for measuring a number of fluorescence-labeled target molecules in the same solution, JP-A No. 528714/2002 discloses a constitution of moving the sample solution or sample solution holding means.

In the case of the constitution disclosed in JP-A No. 528714/2002, since the density of the laser excitation lowers in an inverse proportion with the area of the laser irradiation region to the sample, it is difficult to ensure a wide measuring region while keeping the sensitivity. This is because the incident direction of the laser to the sample solution and the measuring direction of the fluorescence are aligned and extension of the laser irradiation region inevitably lowers the density of excitation intensity. Actually, the laser irradiation region is about from 100 to 10,000 mm$^2$, in Example 1 of JP-A No. 528714/2002. In a case where the laser irradiation region is extended further, SM reduction is lowered and it is difficult for fluorescence measurement from a phosphor or a group of phosphors labeled on one target.

In JP-A No. 21556/1988 to Patent Document 6, it is adapted such that the fluorescence-labeled target molecules separated on every molecular size by electrophoresis can be measured by the fluorescence intensity. Accordingly, when a container (glass plate) holding a sample solution is moved relative to the laser during electrophoresis, information for the molecular size can not be obtained accurately. Further, in a case of electrophoretic measurement, since the fluorescence-labeled target molecule is not a single molecule but a plurality of molecules, fluorescence emission is caused to some extent in a case where there is a density of laser excitation to some extent to give no troubles for the fluorescence detection. However, since the emission of the fluorescence is small in the single molecule measurement using only a small number of fluorescence-labels, it is difficult to attain quantitative determination at high accuracy by the same constitution of laser irradiation as in the case of the electrophoretic measurement.

Further, in JP-A No. 229859/1997, since the object of the disclosed constitution is to measure the life of the fluorescence substance, a pulsed laser is used and the laser in the sample container is propagated through the sample container and the distribution of the fluorescence intensity is measured with lapse of time. Accordingly, in a case where the sample container is moved relative to the laser light, the life time of the phosphor can no more be measured accurately.

Further, also in the constitution disclosed in JP-A No. 513555/1998 and JP-A No. 513556/1998, it is described that the gel is used for conducting electrophoresis and relative movements for the two sheets of glass plates under electrophoresis in the same manner disturbs the information of the separated molecular size in the same manner as in JP-A Nos. 528714/2002, 21556/1988, 134101/1995, 105834/1996, 43197/1997, and 210910/1997.

Finally, JP-A No. 528714/20020 discloses a constitution for fluorescence measurement in which the irradiation direction of the laser and the measuring direction of the fluorescence are in perpendicular to each other. However, in the disclosed constitution, a laser emission device is disposed on an optical analyzing chip and it is difficult to mechanically move the laser light relative to the sample measuring region.

As described above, upon single molecule measurement, it has been difficult to measure a sample in a wide range at a high accuracy for a predetermined time.

The present invention provides means capable of solving the problem that a volume that can be measured for a predetermined time is small in highly sensitive fluorescence measurement, particularly, in single molecule measurement capable of measuring without using chemical amplification.

As a constitution for extending the laser irradiation volume in the propagating direction of a laser, a measuring region is extended without lowering the density of laser excitation. That is, as shown in FIG. 4, a laser light is propagated under multiple reflections between two substrates of a sample holding portion for holding the sample solution (hereinafter simply referred to as a sample container). In this case, samples in the propagating direction of the laser light can be excited at a same time, and fluorescence emitted from the targets present in the region can be photographed at a time. Since the laser light propagates with scarce decay between the two sheets of glass substrates, fluorescence-labeled target molecules in the sample solution can be excited at a sufficient intensity. The light irradiation system is hereinafter referred to as lateral incidence. Further, at the instance the photographing has been completed, the sample container is moved mechanically by a width 117 for the laser spot in the direction of an arrow in FIG. 4 and next photographing is conducted. The measurement volume is extended by repeating the operation. By the lateral incidence and relative and mechanical movement of the laser irradiation region described above, the measurement volume can be extended without lowering the intensity of the fluorescence excitation.

Further, in the measuring method as described above, in a case of measuring samples of an identical volume, the cycle of movement of the sample holding medium can be decreased. This can increase the measurement volume in a certain time, that is, throughputs can be increased. The cycle of movement can be decreased due to the auxiliary improvement of the throughput in addition to the improvement of the throughput due to the extension of the measurement volume for once. This means that a time is required also for the movement of the laser irradiation region, and that the reduction of the moving time is effective for the decrease of the measuring time in view of the entire measuring time. In a case of moving the sample container by the system disclosed in JP-A No. 528714/2002, since the laser excitation direction and the fluorescence measuring direction are aligned, the density of excitation intensity has always to be lowered for extending the measuring region. In the invention, since the excitation laser light propagates inside the container, the measuring region can be extended in the laser propagation direction without greatly lowering the density of excitation intensity. Accordingly, in the constitution described in JP-A No. 528714/2002, since the laser irradiation area is relatively small when compared at an identical intensity of excitation laser, the cycle of movement for the sample container is increased to increase the measuring time. The effect on the throughput in this case, is not only mere increase by p times of the time necessary for measurement and reduction of the throughput by a rate of p when the measurement volume is increased by p times by the movement of the sample container by p cycles. Since the time concerning the movement of the sample is added on every measurement for once, the entire excess time regarding the movement of the sample increases in proportion with the cycle of the movement to further lower the throughput.

In accordance with the invention, by holding a sample solution between two substrates and mechanically moving the same, a solution in a wide range can be measured simply to improve the throughput. A fluorescence detection apparatus according to the invention may also comprise, as an example, a first substrate and a second substrate, and comprise a sample holding portion for holding a sample, a light irradiation portion for irradiating excitation light between the first substrate and the second substrate, a detection portion for detecting the fluorescence generated inside the sample holding portion, and moving means for relatively and mechanically moving the sample holding portion relative to the detection portion.

In another constitutional embodiment of the fluorescence detection apparatus according to the invention, the first substrate and the second substrate may have a first layer and a second layer respectively to each of opposing surfaces, and the first layer and the second layer may have a higher refractive index than that of the sample.

In a further constitutional embodiment of the fluorescence detection apparatus according to the invention, the first substrate and the second substrate may have a first dielectric film and a second dielectric film respectively to each of the opposing surfaces, and the first dielectric film and the second dielectric film may have a refractive index higher than that of the first substrate and the second substrate.

A micro-amount of target molecule in a sample solution can be determined quantitatively in a short period of time without using chemical amplification.

DETAILED DESCRIPTION OF THE PREFERRED EMBODIMENTS

Figure 1:
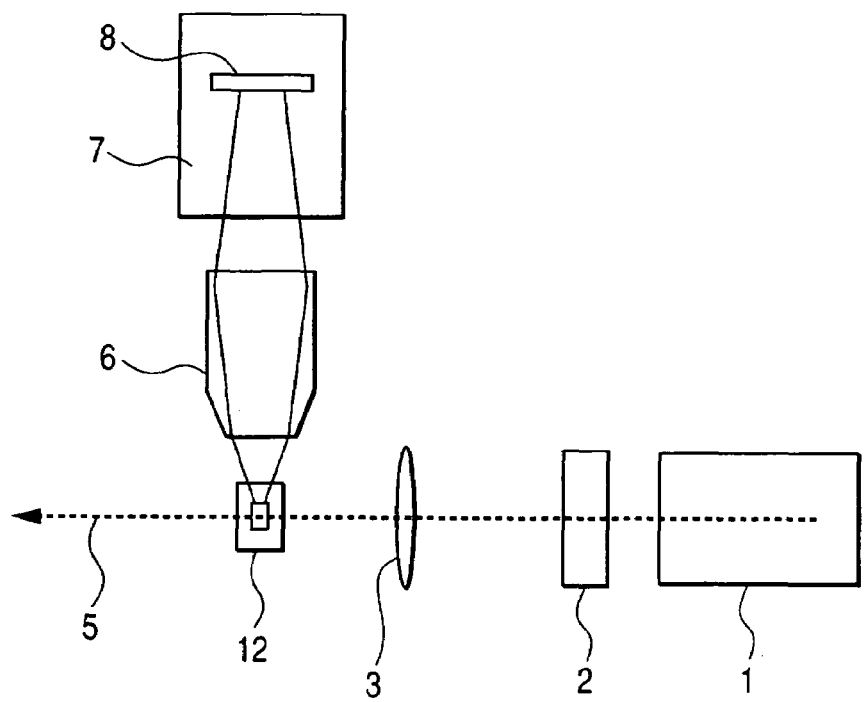
FIG. 1 is a constitutional view of a detection system for practicing an existent method.
Figure 2:
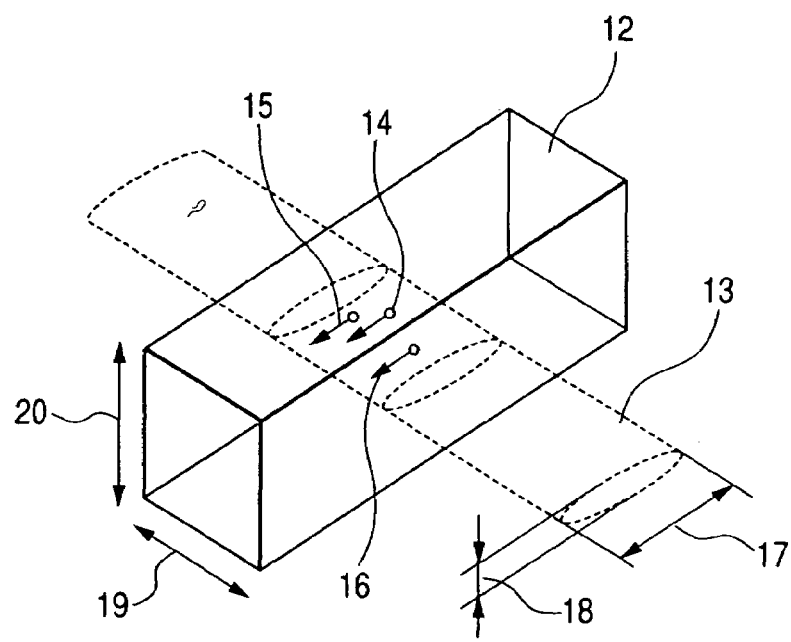
FIG. 2 is an enlarged view for a region of a capillary irradiated with a laser light.
Figure 3:
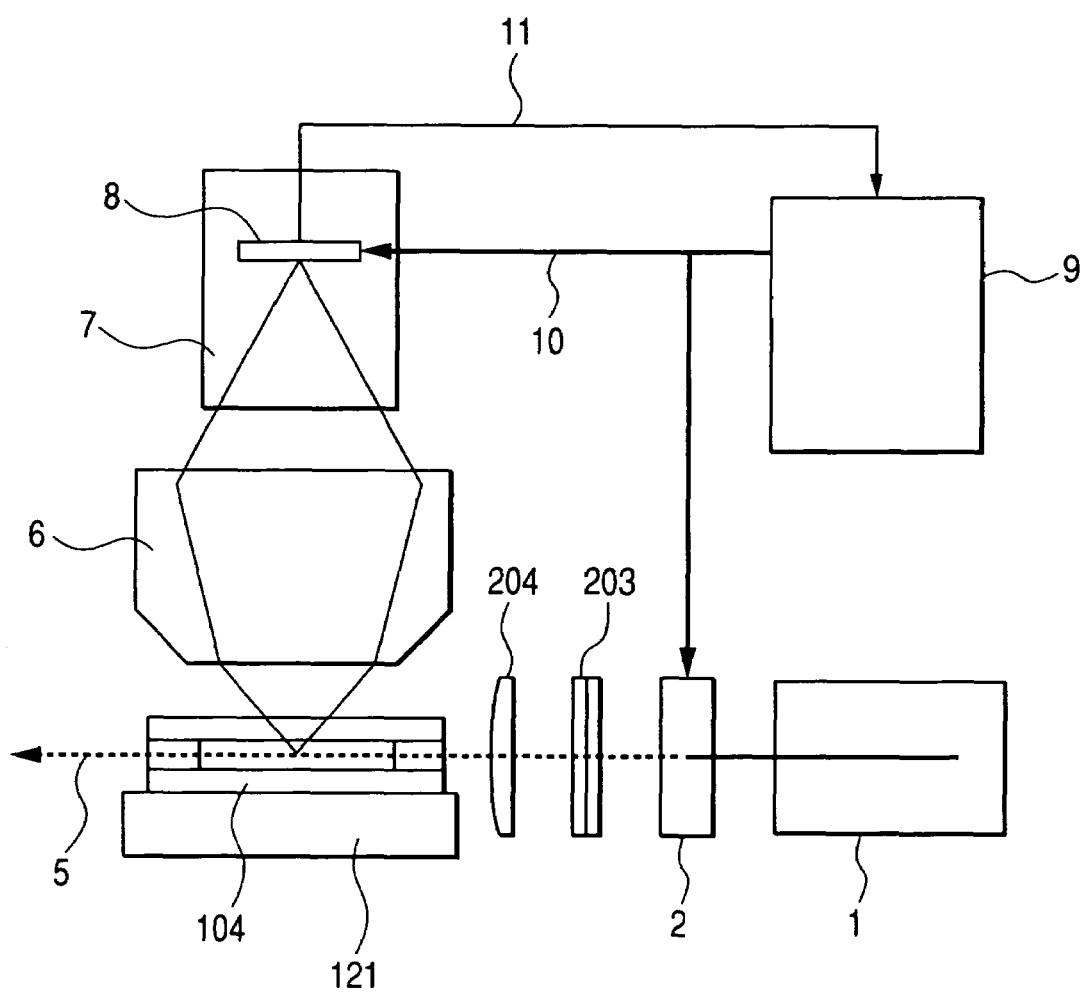
FIG. 3 is a fundamental constitutional view of an apparatus according to the invention.

FIG. 3 shows a basic constitution of the present invention. A light from an $Ar^+$ light source 1 oscillating an linearly-polarized light is irradiated to the inside of a sample container 104 holding a sample solution, and fluorescence from a labeled target molecule is measured by CCD 8. At first, an exposure time is properly controlled and two cylindrical lenses of different focal lengths are used such that the spot size of the modulated laser light is reduced in the direction of the container thickness (direction of z axis) into an elliptic shape at the end face of the container 104. A first cylindrical lens 203 defines a laser width 117 in the direction measuring volume with the container 104. A cylindrical lens 204 defines a laser spot width 118 in the direction of the container thickness. The focal distance of the lens is shorter than the focal distance of the cylindrical lens 203. This forms the shape of the laser spot to an elliptic shape at the incident position to the container. The laser beam incident to the container propagates under multiple reflections between the two quartz glass plates 130 and 132 and excites the phosphor of the target in the sample solution held between the two quartz glass plates. The generated fluorescence is collected by an objective lens 6 and focused on a CCD 8. Then, a trigger signal for exposure is sent by way of a signal line 10 to the CCD in synchronization with the excited laser modulation signal to the shutter 2. Fluorescence images processed in the CCD 8 and a CCD camera 7 are transferred byway of an image signal line 11 to a control system 9. Further, the control system 9 generates a trigger signal for exposure which is sent to the signal line 10 in accordance with the time taken into 1 frame (image). Further, a driving signal is sent from the control system 9 in synchronization with the time of frame simultaneously to a mechanically transferred stage 121 to transfer the sample container 104 by the laser width 117 in the direction of scanning shown in FIG. 4. The transferring mechanism is moved by using a stepping motor and controls the action of the stage such that a large acceleration as transferring the fluorescence-labeled target molecule in the laser irradiation region is shifted to the outside of the irradiation region by the acceleration applied to the sample solution at the start or completion of transfer. Further, upon measuring the fluorescence, the stage is stopped such that the fluorescence spot is not blurred. In this case, as shown in FIG. 5, a driving signal is prepared such that the time of stage transfer and the exposure time for laser excitation do not overlap. This can shorten the time of transfer of the sample container to improve the throughput.

Further, lens of a high magnification is used for the objective lens so as to take the fluorescence as much as possible. For this purpose, the focal depth (thickness of solution capable of finely obtaining images) is as small as several millimeters to several tens of millimeters. In order to increase the ratio of fluorescence-labeled target molecules that can be measured in the container, the thickness of the container has to be decreased. On the other hand, since the throughput is in proportion with the area that can be measured at a time as described above, it is preferred that the width 117 of the input laser in the direction parallel with the substrate is larger and the thickness 118 in the direction of the thickness of the substrate is smaller. Accordingly, it is preferred that the beam shape of the incident laser light is elliptical. For the beam shape, it may be controlled such that the beam (excitation light) at the center of the sample container is larger in the horizontal diameter than in the perpendicular diameter to increase the irradiation efficiency.

Figure 6:
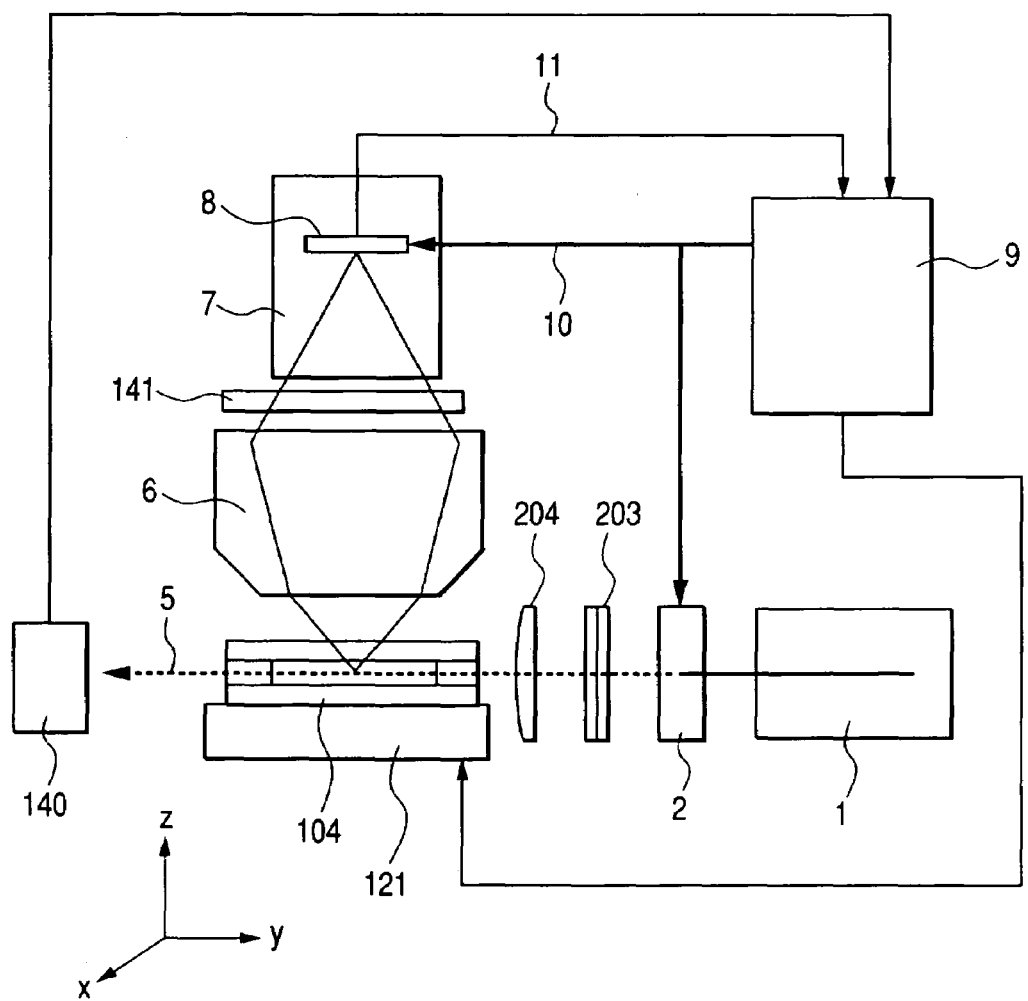
FIG. 6 is a schematic perspective view for the constitution of an apparatus in a preferred embodiment and Example 1 of the invention.

Then, the sample container 104 is to be described. As shown in FIG. 6, two spacers 133 are formed between a first substrate 131 and a second substrate 132 and a solution having a thickness of the spacer is held between the two substrates. A quartz substrate is used for the first and the second substrates. The thickness of the spacer is 25 mm and the spacer is formed by dry etching a polyimide or quartz glass. As the material, quartz less causing fluorescence is more preferred. A cover 135 made of glass or PDMS (polydimethylsiloxane) is bonded so as to prevent the held sample solution to the control 104 from being rounded by the surface tension at the input portion and the output portion of the laser light and scattering the light. For the bonding, a UV-cure adhesive is used in a case where the cover is made of glass and adhesiveness with glass is utilized in a case where it is made of PDMS. The cover is in contact with at least a portion of the wall surface of the sample container along the incident direction of the beam. In this example, a plate-like member covering the wall surface in the incident direction of the beam of the sample container is used. Without the cover, the sample solution forms a concave or convex shape at the end face of the sample container (at a position for bonding cover 135) by the surface tension to scatter the incident laser light. The cover is provided for efficient incidence of the light into the sample container with no such disadvantage. Particularly, by the use of PDMS, the adhesive penetrates by capillarity between the substrates 132 and 231 to eliminate the possibility of forming a scatterer for the laser light. Accordingly, the manufacturing yield for the sample container can be improved.

Then, a sample labeling method for quantitative determination is to be described. At first, a molecular beacon probe is hybridized to a target molecule. In order that the molecular beacon probe emits fluorescence, it is necessarily hybridized to the target molecule to increase the distance between a phosphor and a quencher labeled to the 3'-end and 5'-end of the probe respectively. This is because fluorescence from the phosphor is suppressed in a case where the quencher is close to the phosphor by the fluorescence energy transfer, but the efficiency of the fluorescence energy transfer is gradually decreased as the distance between the phosphor and the quencher increases. Specifically, a molecular beacon probe solution at $10^{-5}$M is admixed to a sample solution such that the final concentration is $10^{-7}$ to $10^6$ M. Since the unreacted molecular beacon probe dose not cause emission by the fluorescence energy transfer, it gives no effects on the measurement. The number of molecules of the molecular beacon probe emitting fluorescence is increased in accordance with the concentration of the target molecule.

As the probe for recognizing the target, a branched DNA probe, a probe labeled with quantum dot, or a probe labeled with phycoerythrin, etc can be utilized in addition to the molecular beacon probe.

Finally, measuring procedure is to be described. At first, the sample solution prepared by the procedure described above is introduced between the first substrate 131 and the second substrate 132. Then, an excitation light 113 controlled for the spot shape by the cylindrical lenses 103 and 204 is entered between the first substrate 131 and the second substrate 132 in a direction substantially parallel with the substrates. Substantially parallel means herein has such a parallelism within a range that can be regarded as identical with parallelism relative to the substrate. In this case, the fluorescence emitted from the molecular beacon probe is measured by the objective lens 6 and the CCD 8. A date for 1 frame (screen) can be acquired and, when transfer to the control system 9, is completed, the sample container 104 is moved relatively and mechanically to the detection portion in the direction of an arrow 5 or 115 to observe a region of not measured portion. Fluorescence from the molecular beacon probe in the sample solution for a wide range is measured by the measurement for the fluorescence and the scanning of repeating the relative transfer of the sample container 104.

EXAMPLE 1

Figure 7:
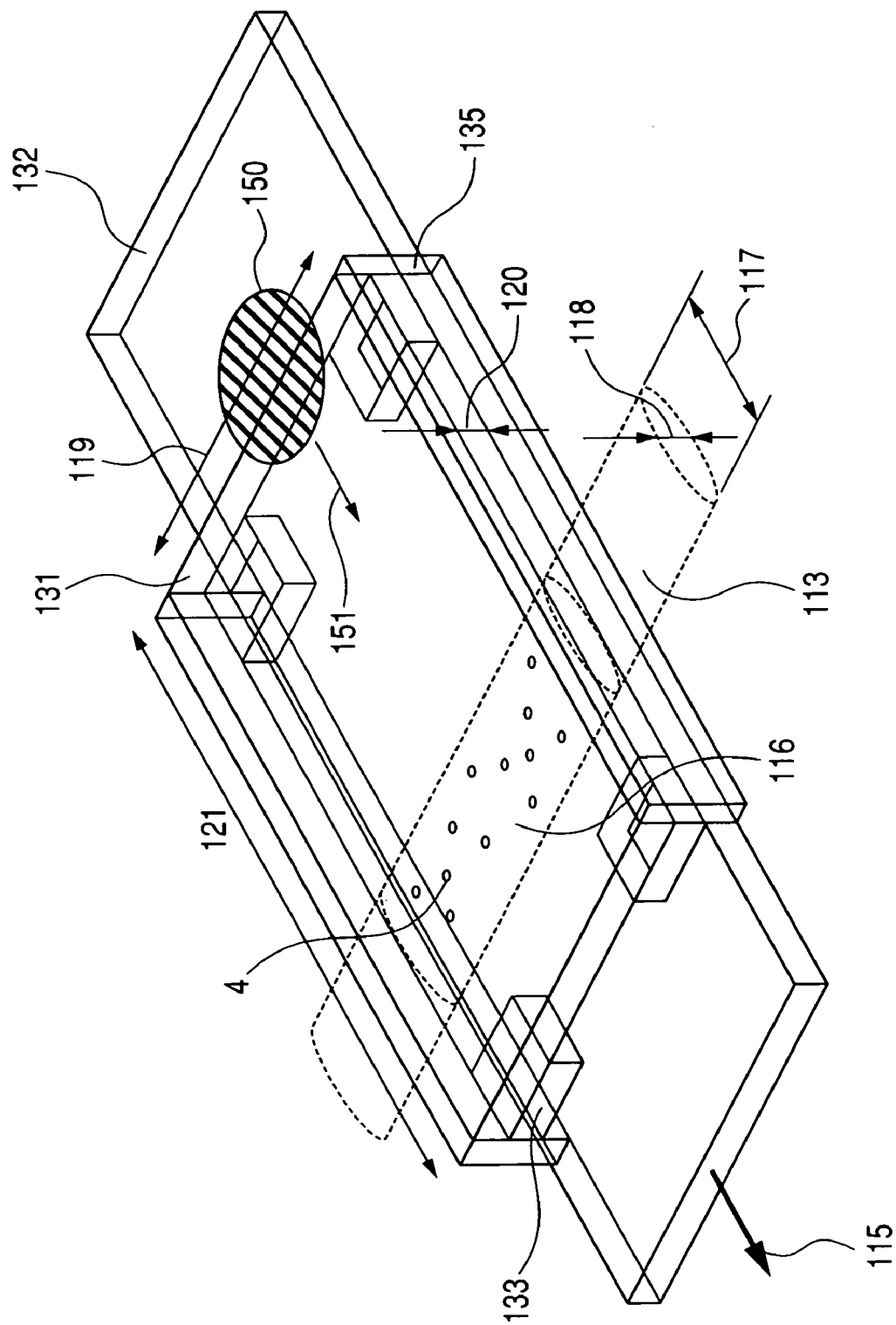
FIG. 7 is a perspective view of a sample holding container in a preferred embodiment and Example 1 of the invention.

At first, a sample container for holding the sample solution is to be described. As shown in FIG. 7, two spacers 133 are formed between two quartz substrate 131 and 132 and a solution having a thickness of the spacer is held between the two substrates. The substrate is attached or not attached with a low refractive index film. In this example, description is to be made to a case of not attaching the film.

Figure 8:
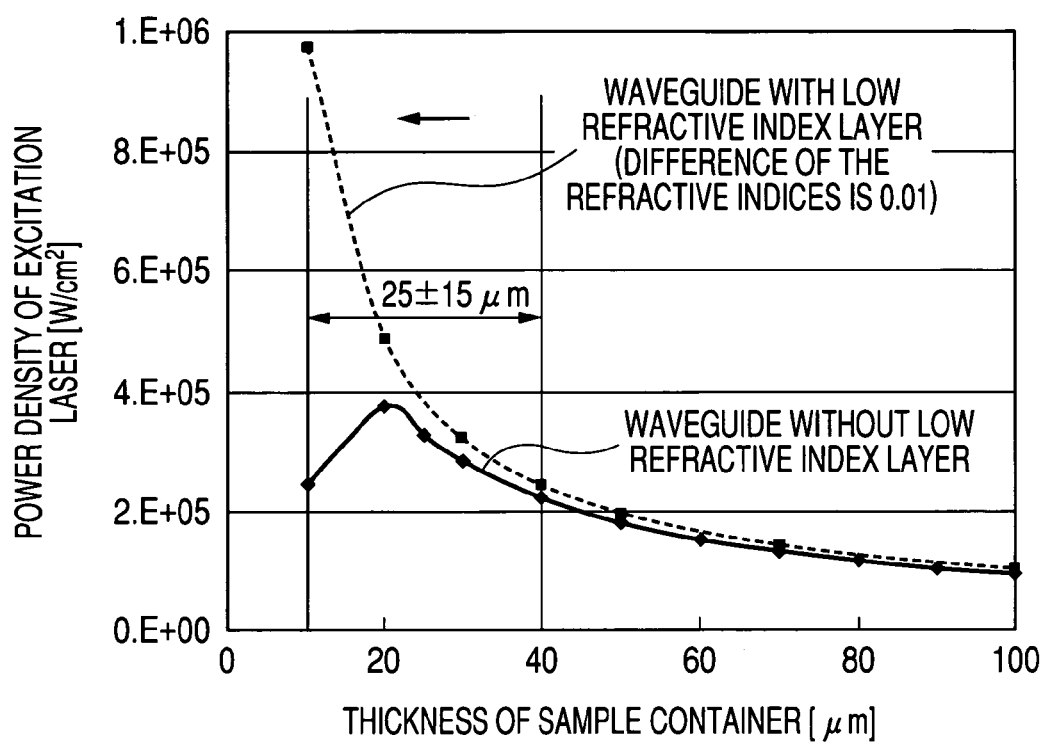
FIG. 8 is a graph showing a relation of a distance between two substrates (thickness of solution) and a density of light intensity.

The optimal spacer thickness is to be described with reference to FIG. 8. The graph shows mean values for the density of excitation intensity in a case of changing the thickness of the spacer, that is, the thickness of the solution and setting the laser intensity input to the sample container constant at 10 mW. The solid line shows the dependence of the density of excitation intensity on the thickness of the spacer in this example with low refractive index thin film. It is assumed that the solution is purified water (refractive index: 1.33). In a case where the thickness of the spacer is 40 μm or more, the density of excitation intensity lowers as the thickness increases. This is because the spot size is extended irrespective of the incidence of laser at a constant intensity. On the other hand, the density of excitation intensity is lowered greatly also in a case where the thickness of the spacer is 20 μm or less. This is because the ratio of reflection light increases effectively as the thickness of the solution lowers at a large angle to the boundary between the solution and the glass to lower the reflectance at the boundary. In this example, 25 μm thickness is adopted as an intermediate thickness between both of the effects. A preferred thickness as the distance between the two substrates is 25±15 μm at which the density of excitation intensity does not lower to ½ or less.

FIG. 6 shows a constitutional view for the detection system. A light from an Ar$^+$ laser light source 1 at an oscillation wavelength of 488 nm is irradiated to a sample container 104, and fluorescence is measured by a cooled CCD 8 of 512×512 pixel. The basic constitution is identical with that of the optimum embodiment for practicing the invention as described above. A cylindrical lens 203 for condensing the laser light defines a spot width 117 in the horizontal direction and the focal distance is set to 150 mm. Further, a lens 204 defines a spot width 118 in the perpendicular direction and the focal distance is set to 25 mm. The mean light intensity just before the sample container is set to 10 mW. The objective lens has a magnification of 20× and a numerical aperture (NA) of 0.75. Further for eliminating scattered light, a notch filter 141 for the excitation light wavelength 488 nm as the center is inserted between the CCD camera 7 and the objective lens 6.

Then, the driving method for the sample container 104 is also identical with that described previously. Specifically, the exposure time is set to 10 msec, the data transfer time is set 190 msec, and the sample transfer time is set 150 msec. FIG. 5 shows a time chart. 1 frame time is determined by the exposure time and the data transfer time, which is 200 msec. In this example, since the data transfer time can be set shorter than the sample transfer time, increase in the measuring time that increases along with increase of the container transfer cycles is minimized by simultaneously conducting the sample transfer and the data transfer.

Further, capillarity is utilized for the introduction of the sample solution to the sample container 104. In FIG. 7, when the sample solution is dropped to a region 150, the sample solution is introduced by capillarity in the direction of an arrow 151. In this case, openings are necessary for two or more portions in order to vent air in the inside. In a case where the sample container 104 is slanted greatly it may cause a disadvantage that the sample solution flows out. Accordingly, a stage actuator 121 holding the sample container is adapted to keep the sample container substantially horizontal. This means that the two substrates are substantially horizontal. Substantially horizontal means herein a horizontal state that can be regarded horizontal.

Figure 9:
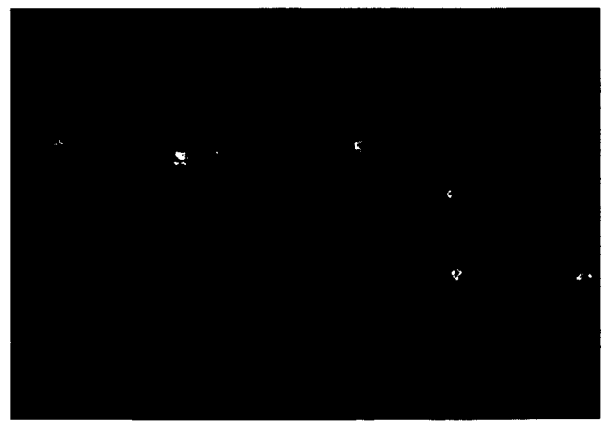
FIG. 9 shows an example of fluorescence molecule images using a sample container.

FIG. 9 shows an image of molecule fluorescence obtained by the constitution shown in this example. The sample is a solution in which double helical DNA of 3.8 kb is labeled with an intercalater YOYO-1 and the DNA concentration is $10^{-12}$ M and YOYO-1 concentration is $10^{-9}$ M.

EXAMPLE 2

This example shows a constitution in which a film is attached to the substrate of the sample container. According to this constitution, since the density of laser excitation can be improved for the identical intensity of laser excitation, the exposure time can be shortened and improvement for the throughput can also be expected.

Figure 11:
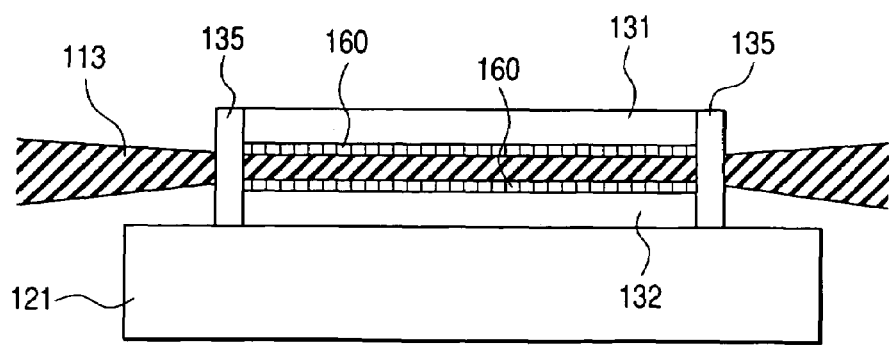
FIG. 11 is a cross sectional view of a sample holding container in Example 2.

FIG. 11 shows a cross sectional structure of a container. As shown in FIG. 11, a solution (sample) is held between two quartz substrates 131 and 132 and a laser beam 113 collected by a cylindrical lens is entered in the solution and excites the fluorescent label during propagation. A thin film 160 at a thickness of about 15 μm and of a refractive index lower than that of the solution is formed between the solution and the quartz substrate in order to improve the density of laser excitation. Specifically, a first layer and a second layer are formed respectively each as a thin film at each of the opposing surfaces of the two substrates. As the material of low refractive index, a fluorocarbon resin is preferred. In this example, an amorphous fluoro polymer (refractive index: 1.29) was used. The range for the refractive index applicable as the material of low refractive index may be smaller by 0.1% than the refractive index of the solution and may be greater than 1. The upper limit of the refractive index depends on the refractive index of the solution. The refractive index of the solution changes about from 1.33 to 1.37 depending on the concentration of a salt or a polymer other than the fluorescence-labeled target molecule. In a case where the refractive index of the solution in the working condition less fluctuates, a film with a refractive index smaller by 0.1% or more than that of the solution to be used is formed and the excitation laser light can be propagated between the two sheets of glass substrates. In a case where the difference of the refractive index is less than 0.1%, it is not practical since the incident condition for the laser is stringent. While a larger difference of the refractive index is preferred since the stability to the change of the refractive index of the solution is higher, since this accompanies light absorption and it is not appropriate for attaining the refractive index of smaller than 1 in the wavelength region used for excitation of phosphor. Actually, a range of refractive index from 1.2 to 1.35 is preferred. The effect of the low refractive index thin film 160 is to be described with reference to FIG. 8. The graph shows mean values for the density of excitation intensity in a case where the laser input intensity to the sample container is made constant at 10 mW relative the thickness of the solution held in the container. The solid line shows a case with no thin film of low refractive index, while the dotted line shows the density of excitation intensity in a case with the thin film of low refractive index. It is assumed that pure water (refractive index: 1.33) is used for the solution. It can be seen that the density of laser excitation improves more as the thickness of the solution decreases. As the density of laser excitation increases, the detection sensitivity for the fluorescence molecule improves more. Further, decrease of the solution thickness can also relatively decrease the effect of background noises other than the fluorescence (scattering due to the Raman scattering of water or scattering of molecule in the solution). In this example, the thickness of the solution held in the sample container (distance between the first layer and the second layer as the thin film of low refractive index) is set to 15 μm. In a case where the thickness of the sample solution decreases excessively, since the laser irradiation volume is decreased and the throughput is lowered, it is desirable that the thickness is 15 μm or more and it is set to 15 μm. However, since the measuring sensitivity of the target is higher as the thickness is smaller, the thickness is determined in view of the balance between on the throughput and the fluorescence intensity of the fluorescence-label depending on the application use.

Figure 16:
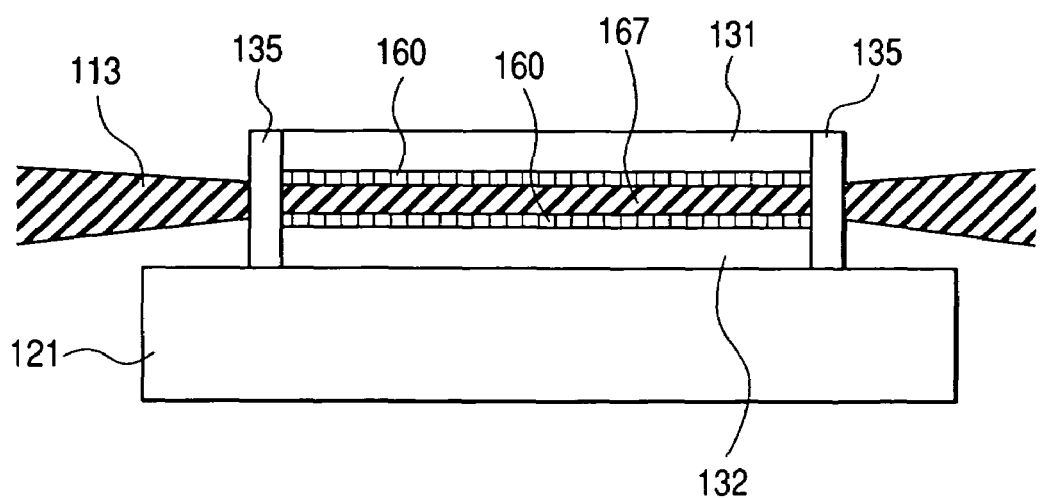
FIG. 16 is a cross sectional view of a sample holding container using a dielectric film as a reflection film.
Figure 17:
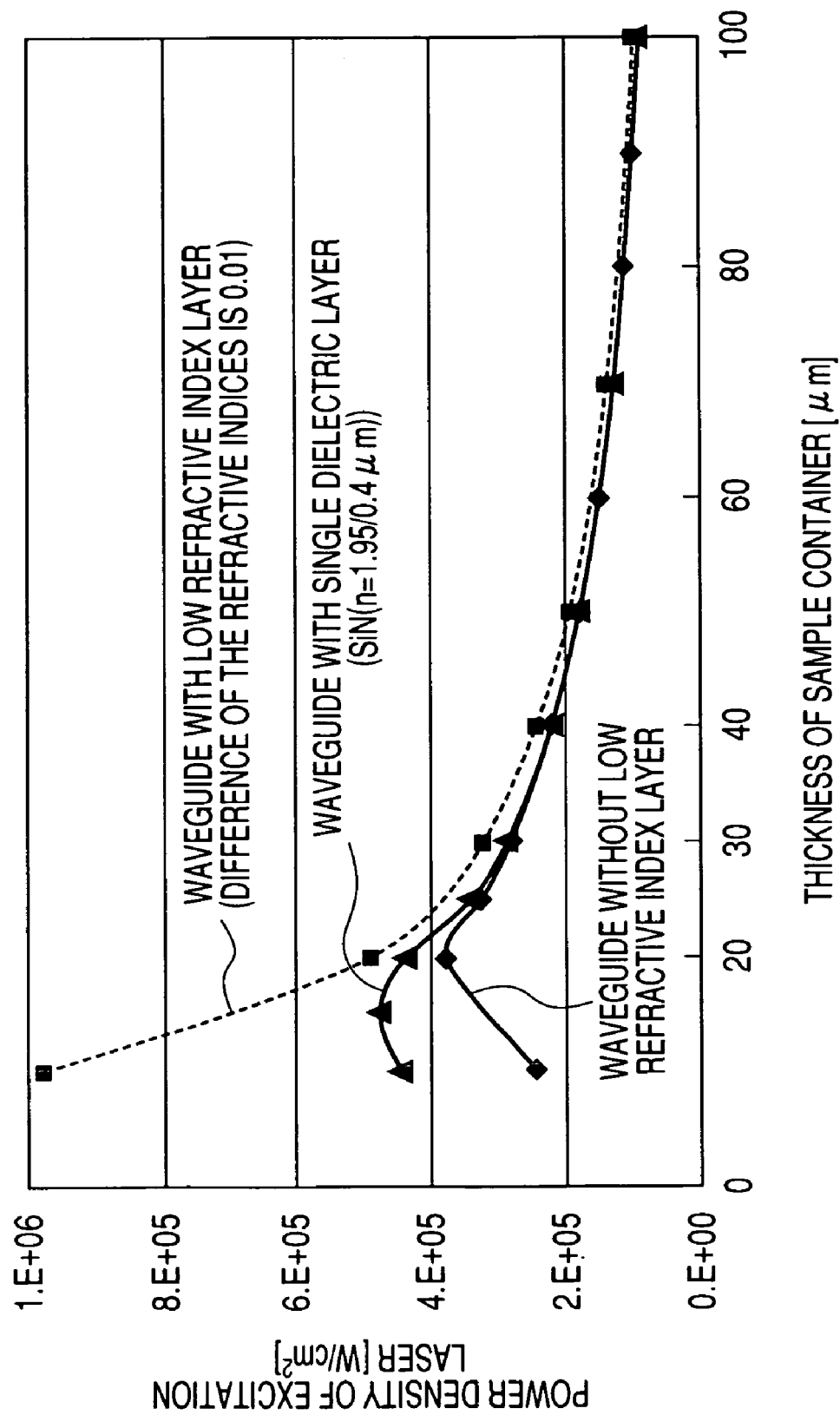
FIG. 17 is a graph showing a relation between the thickness of a solution in the sample holding container using a dielectric film as a reflection film and a density of light intensity.

Further, it is also effective for the improvement of the density of laser excitation by forming a dielectric film (single or multi-layered of dielectric film) instead of the low refractive index film 160 described above, to improve the reflectivity at the boundary between the solution and the glass substrate. FIG. 16 shows a cross sectional view of a sample container using a dielectric (single layer) thin film for the reflection film as a most simple constitution. Instead of the low refractive index thin film (160 in FIG. 11), a dielectric film 166 of higher refractive index than the refractive index of the substrate is formed. That is, a first dielectric film and a second dielectric film are formed each as a thin film on each of the opposing surfaces of the two substrates. With the constitution, total reflection does not occur at the boundary between the dielectric thin film 166 and the solution 167, and a light at a considerably high intensity transmits without reflection. However, since the refractive index of the dielectric thin film 166 is set higher than the refractive index of the glass substrates 131, 132, total reflection occurs at the boundary between the dielectric thin film 166 and the glass substrate (131 or 142). Since the light is reflected with the thickness of the solution 137 being relatively decreased, higher density of excitation laser can be obtained. FIG. 17 shows the density of excitation laser in a case of using SiN (refractive index: 1.95, thickness: 0.4 μm) as the dielectric film by the data depicted with symbol "Δ". As can be seen from FIG. 17, while the excitation density is lower than the case of using the low refractive index thin film, it can be seen that the excitation density improves more than in the case of using only the glass. Since the range of the refractive index of the dielectric thin film has to be higher than the refractive index of the glass as the substrate, it needs a refractive index of 1.45 or more in a case where the index of the glass substrate is 1.45. A favorable intensity of laser excitation can be obtained at the thickness of the sample solution of 15 μm. An optimum range for the thickness of the sample solution is within a range from 10 to 30 μm. Further, it will be apparent that the dielectric film may also be in a multi-layered form. In this case, each of the dielectric films may have a plurality of layers each having different refractive indices and, for example, in a case where each film comprises two layers, the refractive index of the layer in contact with the solution may be higher than that of the layer in contact with the substrate. In a most simple case of the multi-layered structure, an $SiO_2$ layer (refractive index: 1.45) at a thickness of 15 μm as a cladding layer of well controlled refractive index may be inserted between the dielectric film and the substrate. This can obtain more stable total reflection.

Further, as a more complicate case, for example, an SiN layer of 3.6 μm thickness (refractive index: 1.95) is formed at the position 166 on the side of a glass substrate 132, an $SiO_2$ layer of 3.7 μm thickness (refractive index: 1.45) is formed thereon, and the solution is held thereover as shown in FIG. 16. Further, identical two layers are formed being turned upside down on the surface of the upper glass substrate. This can ensure high reflectance of 99% or higher to improve the density of laser excitation. While the example described above shows a reflection film comprising two layers as a multi-layered film, the reflection layer may also be formed by combining more number of layers. The advantage obtained by the use of the dielectric film is to keep the surface in contact with the solution stable and eliminate the possibility of inclusion of unnecessary chemical substances to the sample solution as much as possible.

Figure 10:
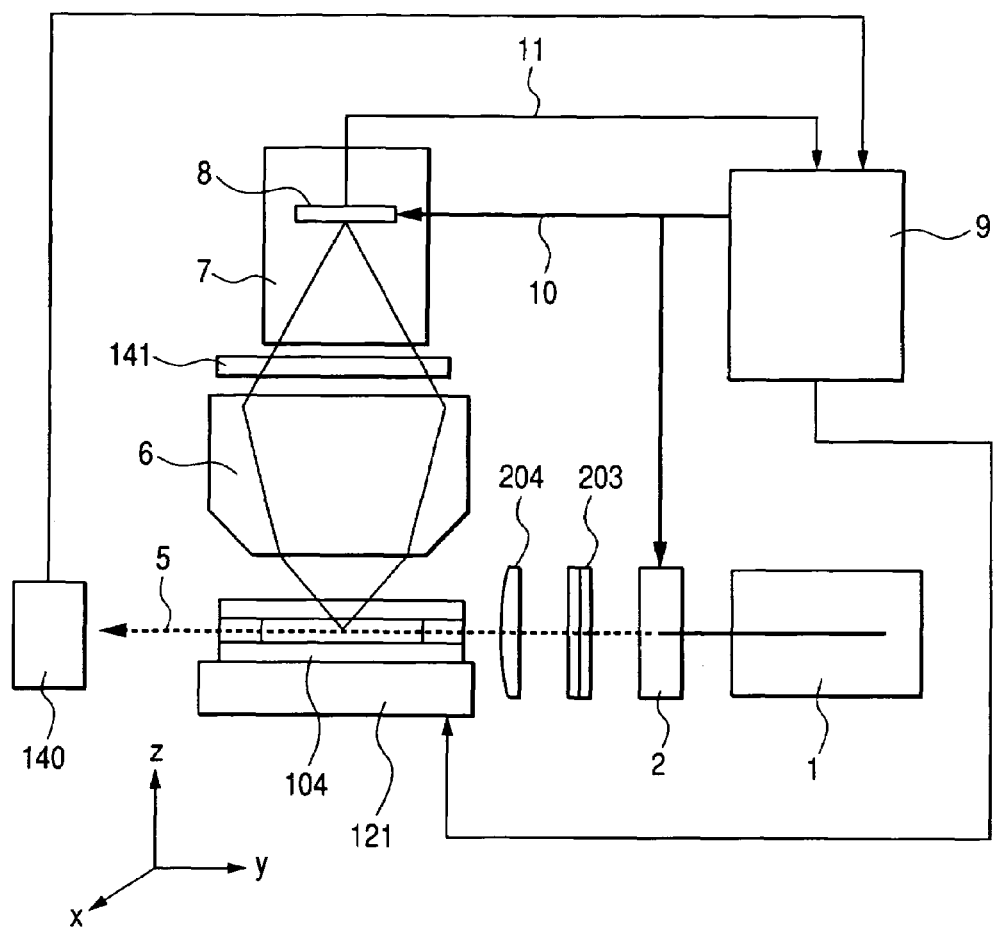
FIG. 10 is a schematic constitutional view of the apparatus in Example 2.

Then, FIG. 10 shows a constitutional view of a detection system. A light from an $Ar^+$ laser light source 1 at an oscillation wavelength of 488 nm is irradiated to a sample container 104 and fluorescence is measured by a cooled CCD 8 of 512×512 pixels. The basic constitution is identical with a best embodiment for practicing the invention described above. For the focal distance of the cylindrical lens that collecting the laser light, the distance for determining a spot width 117 in the horizontal direction of a lens 203 is 150 mm and that of a lens 204 for determining a spot width 118 in the perpendicular direction is set to 25 mm. The mean light intensity just before the container is 10 mW. The objective lens 6 has a magnification of 20× and a numerical aperture of 0.75. Further, for excluding scattered light, a notch filter 141 for an excitation light wavelength 488 nm as the center is inserted between a CCD camera 7 and an objective lens 6.

Then, the driving method for the sample container 104 is also identical with that described above in which the exposure time is set to 10 msec, the data transfer time is set to 190 msec and the sample transfer time is set to 150 msec. Further, it is considered that the container 104 may slightly tilt during he transfer of the sample. Accordingly, it is estimated that the laser spot may be possibly displaced from the optimal position in the perpendicular direction (direction y in FIG. 5). Since the density of laser excitation intensity is lowered in such a case, no accurate quantitative determination is possible. In order to avoid this, a light power meter (light detector) 140 for monitoring the intensity of light passing through the container is disposed in this example and the output of the power meter is output to a control system 9. The control system gives an instruction for positional control to a sample transferring actuator 121 in accordance with the output from the optical power meter. That is, it gives an instruction for controlling the position in the direction Z (direction of the thickness of sample container) in accordance with the output of the light power meter. In this case, the direction Z may be a perpendicular direction. Particularly, in this example, the position in the direction z (direction in the thickness of the sample container) is put to feedback control by the sample transferring actuator 121 such that the output from the light power meter 140 is at the maximum.

EXAMPLE 3

Figure 12:
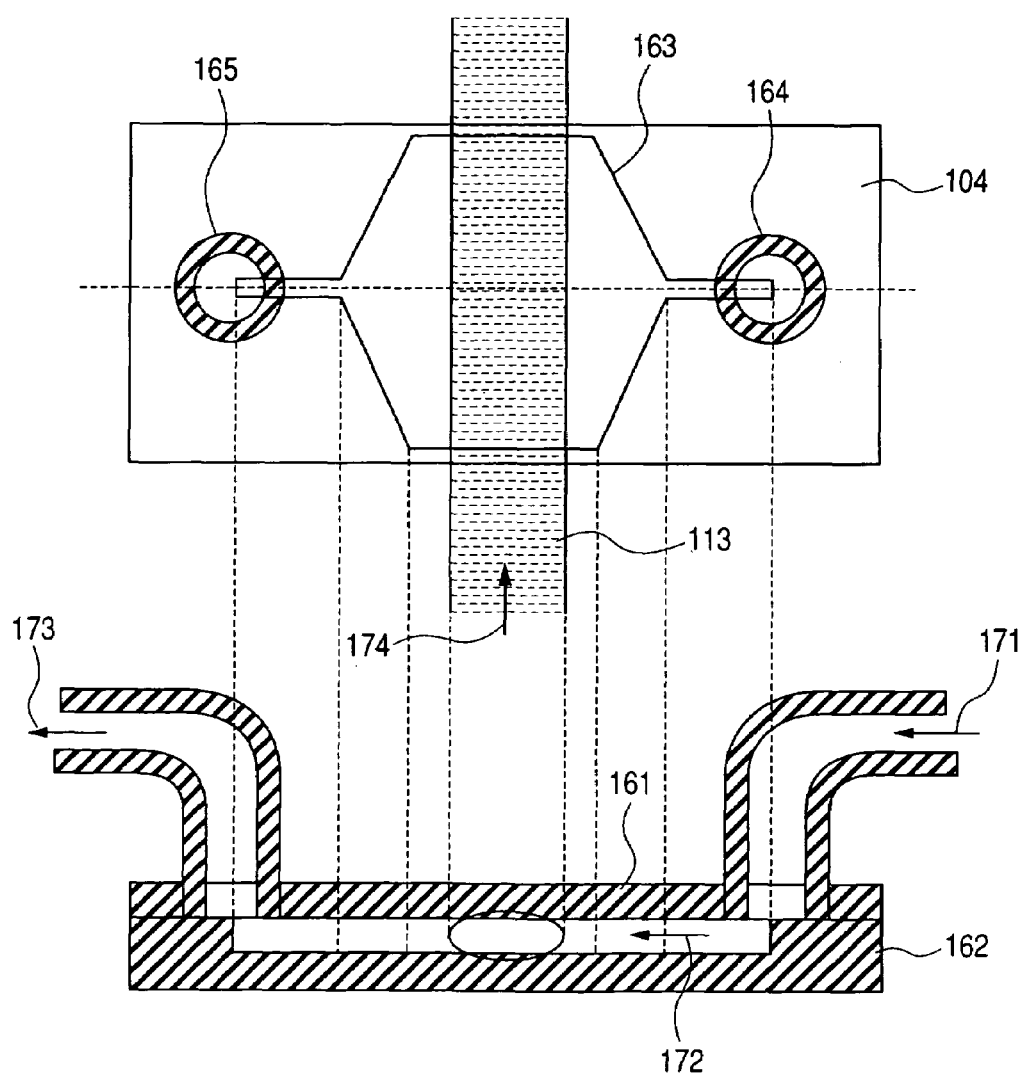
FIG. 12 is a view of a sample holding container in Example 3.

In this example, a flow of a sample is formed to the input and the output of the sample solution by the pressure difference between the input/output portions of the sample solution and the laser irradiation region transfers relatively. A sample container is shown in FIG. 12. In FIG. 12, an upper portion shows an upper plan view of a sample container 104 and a lower portion shows a cross sectional view thereof. The sample container 104 comprises two quartz substrates (first substrate 161 and second substrate 162) in which the lower second substrate 162 has a polygonal indent 163 by dry etching. A sample solution is contained in the indent portion and the sample solution flows. The sample solution enters from an input port 164 and exits from an output port 165. The flow of the sample solution is indicated by arrows 171, 172, and 173.

Further, a laser beam 113 is shaped into a elliptic form using a cylindrical lens and propagates in the solution filled between the substrates 161 and 162 while repeating multiple reflection. The laser beam 113 passes along the wall surface of the indent 163 formed by dry etching, and the etching condition is control such that the etched cross section is planar and vertical so as to sufficiently controlled the scattering of light on the wall surface.

EXAMPLE 4

In this example, an observing region by exposure for once is increased by making the lens constitution different from that of the existent constitution.

Figure 13:
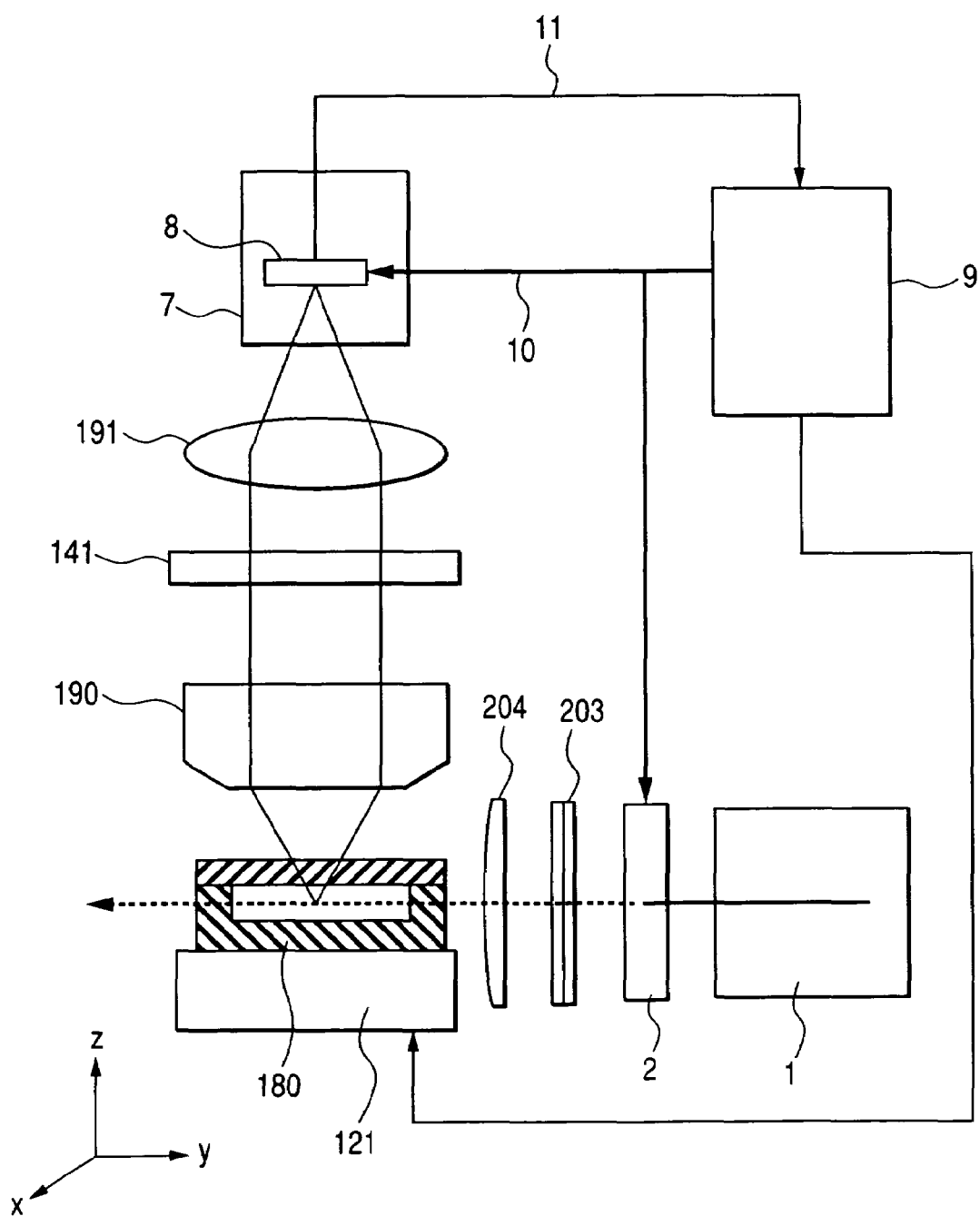
FIG. 13 is a constitutional view of a sample holding container in Example 4.

FIG. 13 shows a constitution of an apparatus according to this example. This is different in the constitution from Example 1 in that two objective lenses are inserted between a CCD 8 and a sample container 104. Usually, NA of an objective lens has to be large for measuring fluorescence. Since fluorescence is emitted isometrically, fluorescence emitted for a wide angle is taken by using an objective lens of large NA. However, in a case of using only one objective lens with large NA for inputting light to a CCD camera 7, the magnification of the optical system increases. This gives rise to a-problem that the observing region for once is narrowed. For overcoming the problem, a first objective lens 190 and a second objective lens 191 are combined. It is adapted such that $NA2>NA1 \times M1$ is established assuming the magnification as M1 and the numerical aperture as A1 for the first lens 190 and the magnification as M2 and the numerical aperture as NA2 for the second objective lens 191. Under the conditions, since the magnification of the two lens system: $M=NA1/NA2$, $M<M1$ is established and the-magnification can be set lower than that in a case of using M1 alone while maintaining the numerical aperture NA1 high, and a observing region for once can be extended. This is a constitution for solving the subject which has been found regarding the constitution for making the high sensitivity and wide observing view field compatible which is, particularly, necessary for the single molecule measurement, and such a subject is not present in existent fluorescence microscope or the like.

EXAMPLE 5

Figure 14:
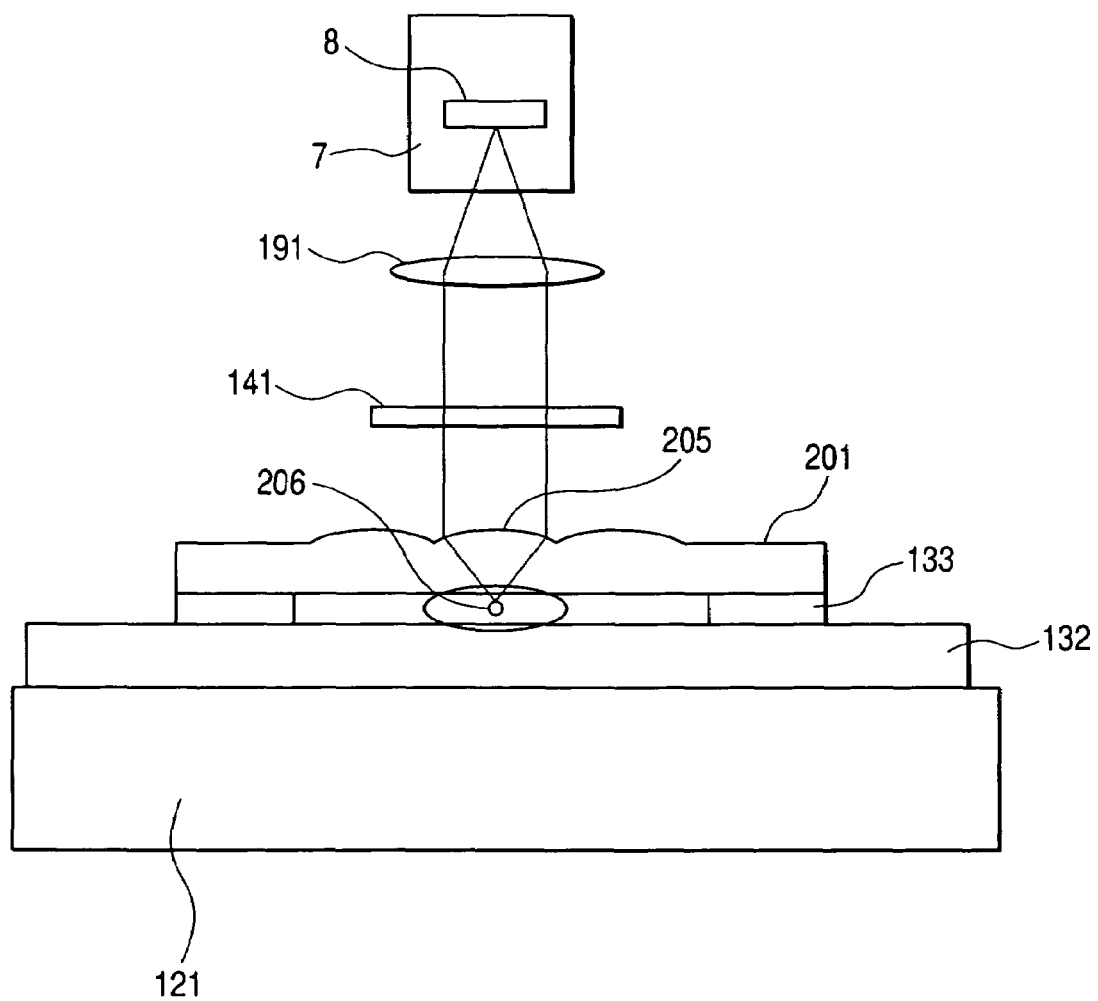
FIG. 14 is a constitutional view of a sample holding container in Example 5.

Also this example has a feature capable of extending the region that can be measured at a time by adopting a different constitution of the lens system. In this example, the first lens in Example 4 is integrated with the container 104 for holding the sample solution, by which fluorescence emitted for a wide angle can be taken and high sensitivity can be attained. FIG. 14 shows a cross sectional view of a sample container taken along the direction in perpendicular to the laser incident direction. The sample container comprises two substrates, and a spacer 133 made of polyimide or quartz is disposed on a substrate 132 below the solution, and an upper glass or substrate 205 with a lens is bonded thereover. In this case, the lens may be formed also by providing a concave/convex portion to the upper surface glass or substrate 205. For the material of the substrate, a polymer material, etc. may also be used so long as the material does not emit fluorescence. A lens-like convex shape is formed periodically on the substrate 205 conforming the view field on the CCD 8 to collect light from fluorescence-labeled molecule 206 and focus the same through the notch filter 141 and the second lens 191 onto the CCD 8. In the constitution, since the first lens formed on the substrate 201 is closer to the fluorescence molecule, a large NA can be obtained. That is, fluorescence can be measured at a high sensitivity.

EXAMPLE 6

Figure 15:
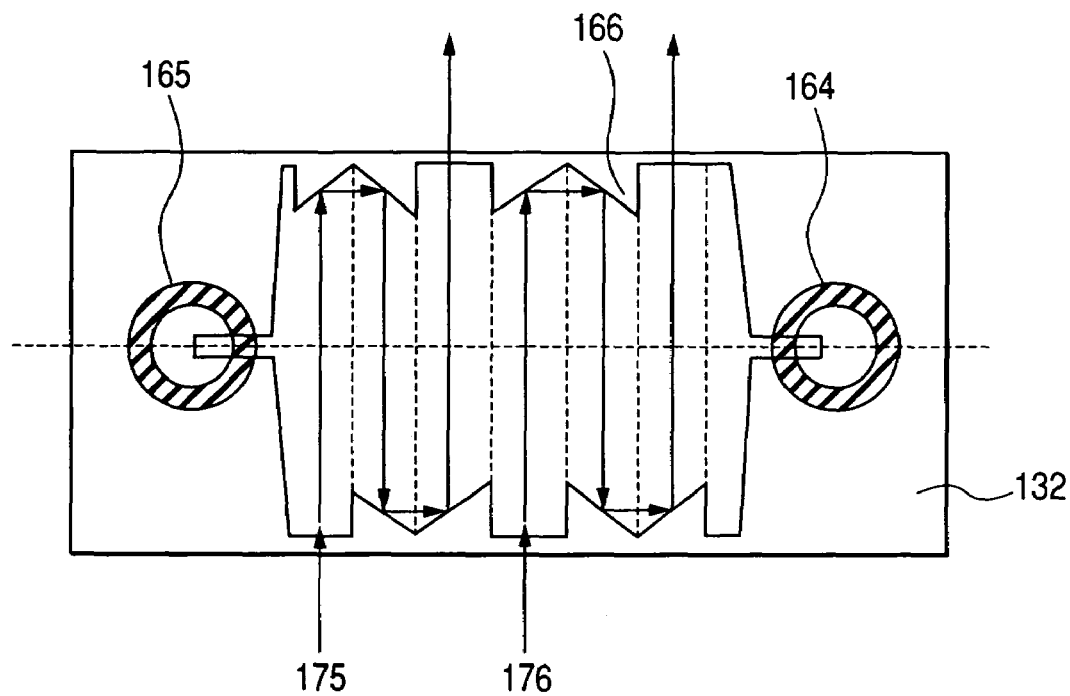
FIG. 15 is an upper plan view of a sample holding container in Example 6.

This example describes an example of extending the laser irradiation volume by reciprocating the excitation laser light in a sample container. FIG. 15 shows an upper plan view in which a reciprocation mirror for laser light is built-in the sample container of Example 3. A region surrounded with a polygon 166 shows a region formed by indenting the surface of a glass substrate 132 by etching. This is different from FIG. 12 corresponding to Example 3 in that the incoming lateral surface and the outgoing lateral surface of laser light each has a chevron shape to form a mirror such that the light propagates in reciprocation as shown by an arrow 175 or 176. With such a constitution, while the laser irradiation region can be extended, phosphors can not be excited uniformly unless loss of the light intensity during propagation of the laser in the sample container is suppressed sufficiently. For attaining this, it is preferred to insert a low refractive thin film 160 or dielectric multi-layered film between the solution and the glass substrate 131 or 132.

EXAMPLE 7

Other fluorescence detection apparatus for improving the throughput may also adopt a constitution including a first substrate and a second substrate, a sample holding portion for holding a sample solution between the first and the second substrates, a liquid control portion for controlling the flow of the sample solution in the sample holding portion, a light irradiation portion for irradiating excitation light between the first substrate and the second substrate, and a sensor provided in a one-dimensional form for detecting fluorescence generated inside the sample holding portion.

Figure 19:
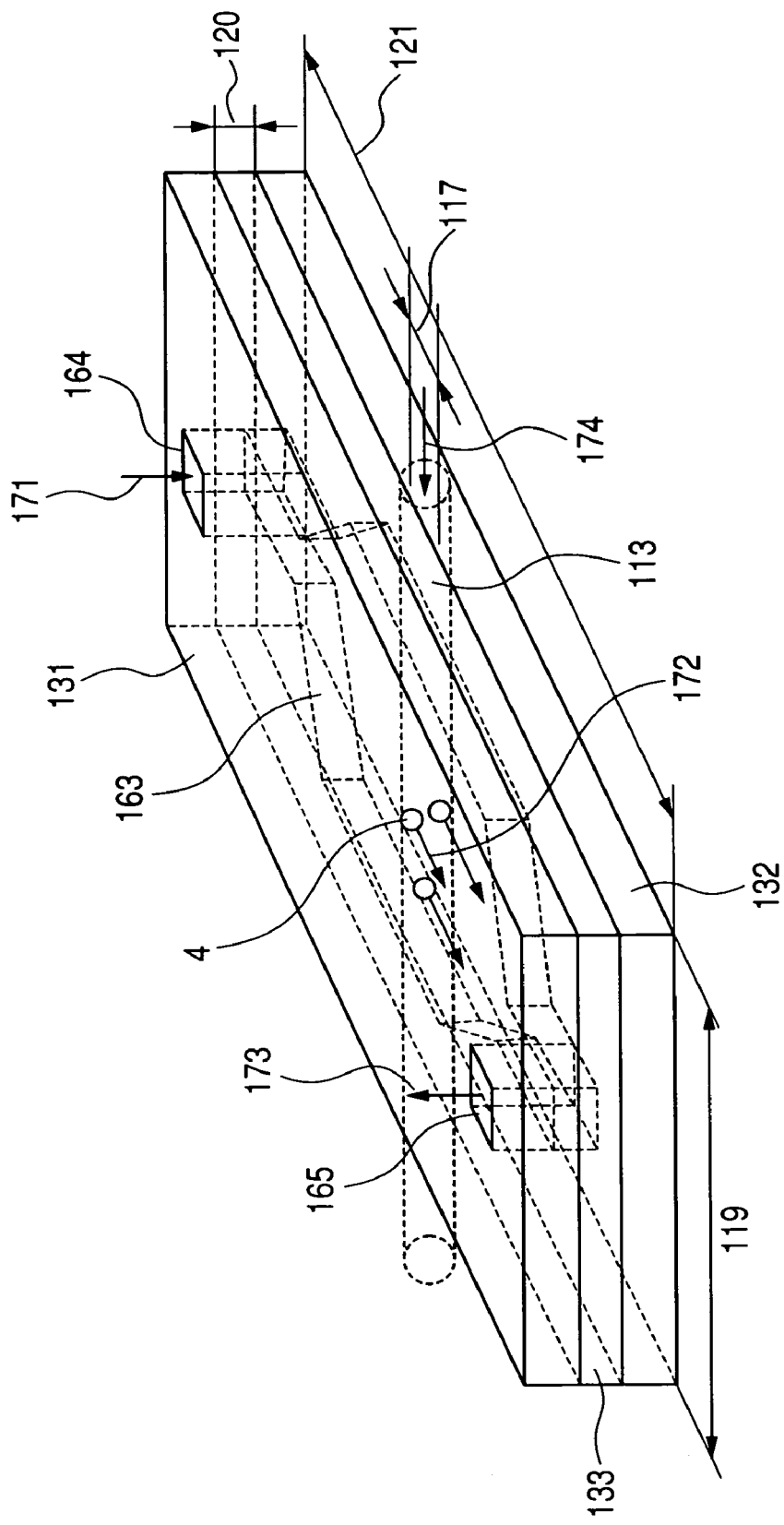
FIG. 19 is a perspective view of a sample flow container using a sample flow container and a line sensor in the best embodiment and Example 7 of the invention.

This is a fluorescence detection apparatus including a sample flow channel portion (hereinafter referred to as a sample flow container) as shown in FIG. 19 instead of the sample container shown in FIG. 4, a line sensor as a one-dimensional light detection device instead of the two-dimensional CCD 8 and a counting portion for the number of fluorescence-labeled target molecules for counting the number of fluorescence spots corresponding to fluorescence from every fluorescence-labeled target molecules. Also this embodiment comprises a constitution of extending a laser irradiation volume in the propagating direction of laser and extending a measurement region without lowering the density of laser excitation.

It has a feature in counting the number of fluorescence-labeled target molecules in a sample solution by flowing a sample solution instead of mechanically transferring the sample container and measuring fluorescence images formed approximately (substantially) from a one-dimensional region in the sample flow container by a line sensor instead of two-dimensional images. By the use of such constitution and measuring method, since the transfer speed of the fluorescence-labeled target molecule in the sample solution can be improved without lowering the measuring sensitivity for fluorescence, throughput can be improved further.

The reasons for improving the throughput are to be described below. Since it is not necessary for mechanically transferring the sample flow container, the transfer time for the sample container as shown in the time table of FIG. 5 is not necessary. Further, since fluorescence images from the one-dimensional region obtained by the line sensor can be transmitted substantially continuously by way of the signal line 11 to the control system 9, a time substantially identical with the measuring time can be allocated as the exposure time, with no loss in view of time. Further, since the laser light acquires fluorescence from the substantially one-dimensional region corresponding to the measurement region by the line sensor, the laser width 117 can be narrowed to improve the density of laser excitation. The fluorescence intensity from the fluorescence-labeled target molecule can be increased in inverse proportion with the laser width 117. Therefore, it is possible to shorten the exposure time. Accordingly, it is possible to improve the problem regarding the method described, for example, in the "Analytical Chemistry", vol. 74, No. 19 (2002), p. 5033 that may possibly be caused in a case of increasing the electrophoretic speed that a fluorescence-labeled target appearing dotwise so far flows and appears as a bar-shape to lower the fluorescence intensity per 1 pixel that can be measured and, accordingly, it is no more possible for measurement. Since the degree of the improvement is substantially in proportion with the exposure time, it is possible to increase the throughput in inverse proportion with the laser width.

Figure 18:
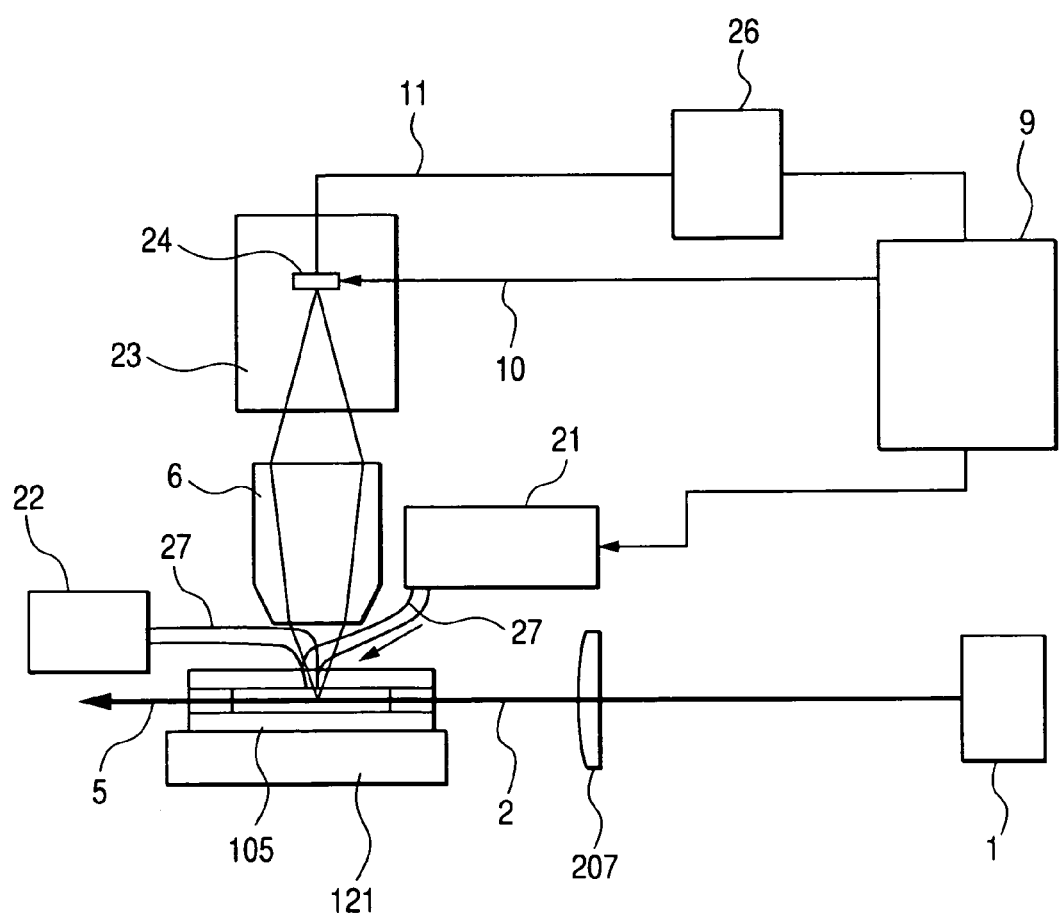
FIG. 18 is a constitutional view of a fluorescence detection apparatus using a sample flow container and a line sensor in a best embodiment and Example 7 of the invention.

A best embodiment for practicing the invention regarding this constitution is to be described. FIG. 18 shows a basic constitution of this embodiment. This is different from the embodiment described previously in measuring the fluorescence from labeled target molecule by using a line sensor, specifically, cooled one-dimensional CCD 24 with a lower noise than that of other line sensors instead of the two-dimensional CCD 8. In this case, for attaining substantially continuous exposure, control for the timing and the length of the exposure time is performed through a signal line 10 from a control system 9 not by using a shutter. Further, since the labeled target molecules 4 are excited in the one-dimensional region to be photographed by using one dimensional CCD camera 23 with an $Ar^+$ laser 1, it is not necessary that the beam shape of the excitation laser is extended in the direction parallel with the transferring direction of the fluorescence-labeled target molecules and the shape may be circular instead of elliptic. Accordingly, an $Ar^+$ laser light is collected by a single lens. For further improvement of the throughput, the spot shape of the excitation laser is preferably formed into an elliptic shape having a major axis in the direction of the thickness of a sample flow container 105. In this case, two cylindrical lenses may be used, and the two cylindrical lenses 203, 204 in FIG. 3 may be rotated by 90°.

Figure 4:
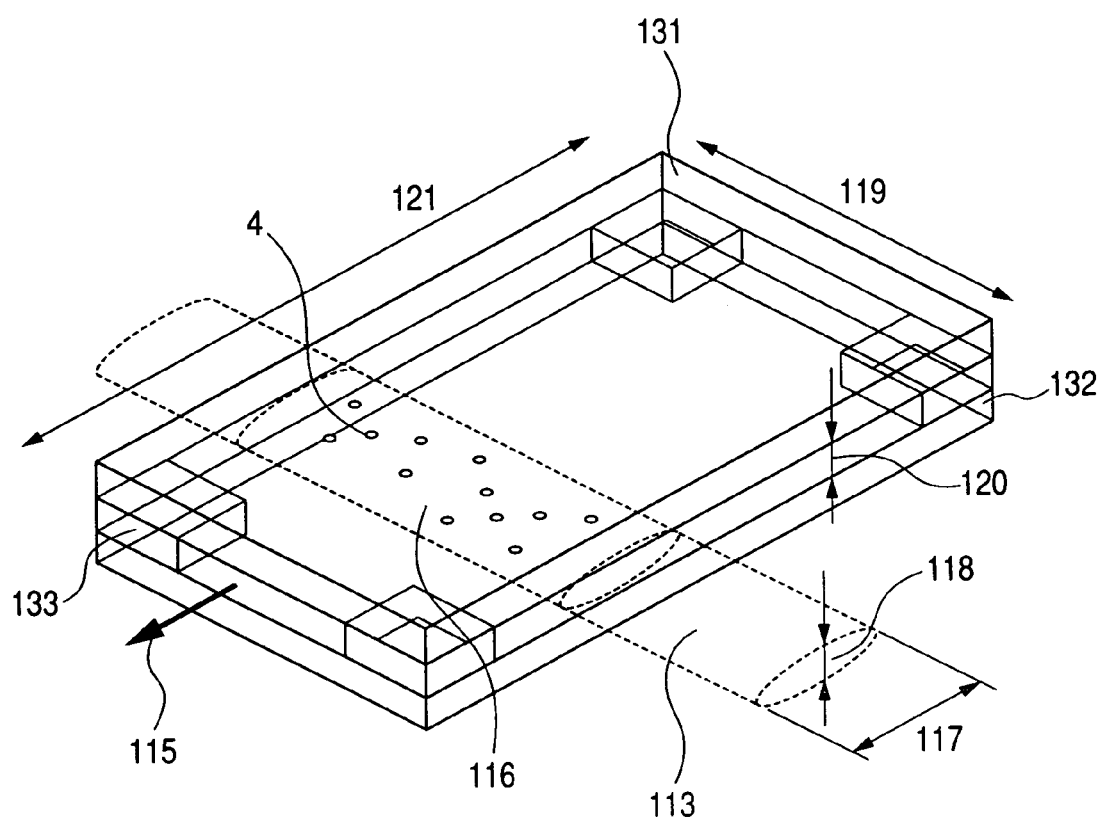
FIG. 4 is a perspective view of a container for holding a sample according to the invention.
Figure 5:
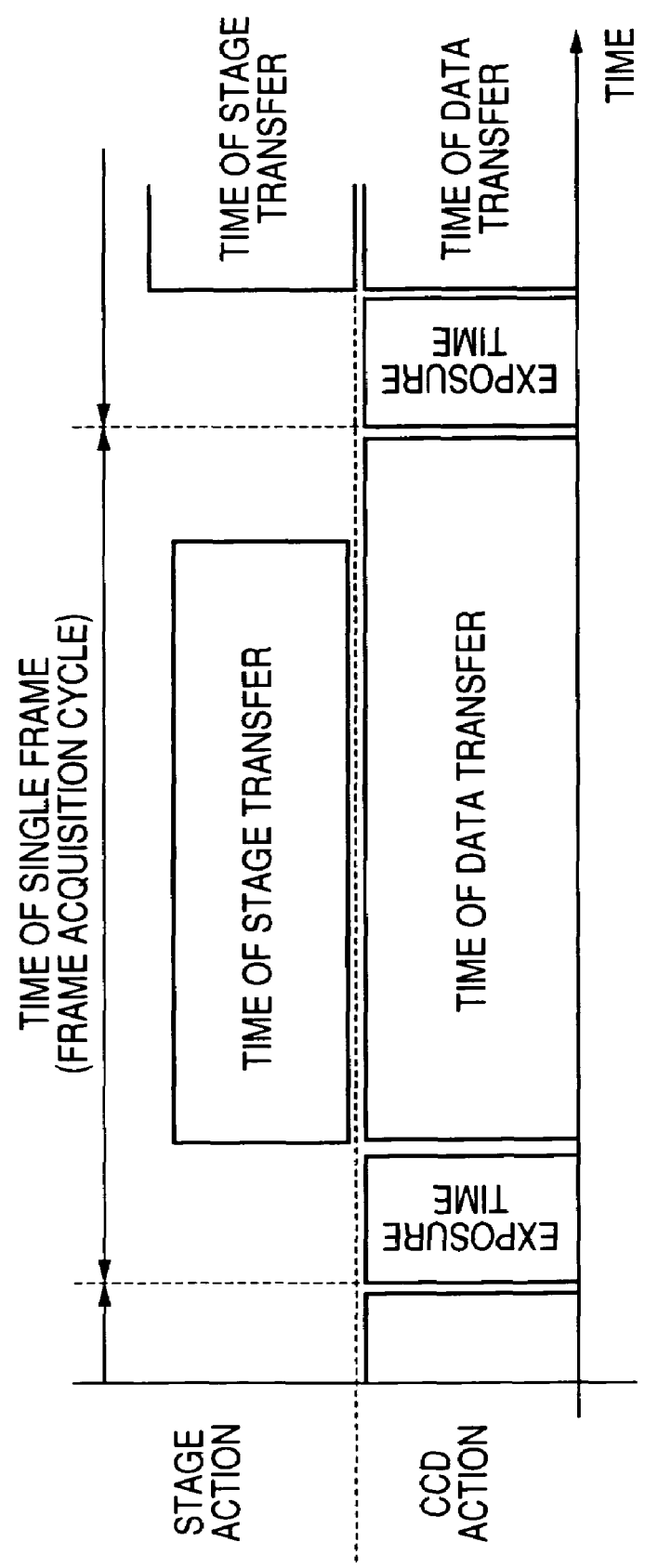
FIG. 5 is a time table for sample transfer time.

A sample flow cell 105 shown in FIG. 19 comprises two quartz substrates 131 and 132 like that in FIG. 4. Further, laser light incident to the sample flow container 105 propagates under multiple reflection between the two quartz substrates 131, 132 to excite phosphors bonded with the fluorescence-labeled target molecules in the sample solution flowing between the two quartz substrates. This can attain the extension of the irradiation region in the direction of laser propagation. Generated fluorescence is collected by an objective lens 6 and focused on a one-dimensional CCD 24. It is adapted that the pixels of the linear CCD 24 are disposed substantially in parallel with the direction of the irradiation axis of the excitation laser, such that the pixels are arranged to the one-dimensional CCD 24 substantially perpendicular to a transferring direction 172 of labeled target molecules 4. The labeled target molecules are controlled by a liquid control portion 21 comprising a syringe and a syringe pump such that they flow at a constant flow speed in a sample flowing channel portion 163. With such a constitution, images for the distribution of fluorescence intensity from the fluorescence-labeled target molecules are continuously acquired by the two-dimensional CCD 24 with no loss in view of the time, and the image for the distribution of two-dimensional fluorescence intensity (hereinafter referred to as 2-dimensional fluorescence images) are reconstituted by data synthesis means of conducting a processing of arranging the one-dimensional images in a time sequential manner. From the obtained two-dimensional fluorescence images, the number of fluorescence-labeled target molecules is counted by a particle counting portion 26, and the concentration of the target molecules is measured based on the ratio of the volume of the sample solution passing through the sample flow content and the number of fluorescence-labeled target molecules that can be measured. Further, the labeled target molecules after completion of the fluorescence measurement are passed through the sample flow container and recovered in a liquid waste reservoir 22.

The constitution of the sample flow container is to be described specifically. Spacers 133 are inserted between the two quartz substrates 131 and 132 for forming a flow channel. The spacer is also made of quartz and serves as a window for irradiating an excitation laser light to the sample solution and serves as a wall not leaking the sample solution. Usually, the spacer can be prepared with good controllability by eliminating a flow channel portion 163 for flowing the sample solution from the lower quartz substrates by etching. It will be apparent that the spacer 133 may be prepared as a separate member and subsequently bonded with the two quartz substrate 131 and 132. One of the two quarts substrates is perforated for forming an inlet 164 and an exit 165 of the sample flow channel portion. Further, the width 119 of the sample flow container is largely extended for the laser irradiation region, for example, compared with the case of the "Analytical Chemistry", vol. 74, No. 19 (2002), p. 5033. Accordingly, it is set to several mm or more. Further, since the length 121 of the sample flow container 105 can be decided irrespective of the sample volume to be measured, it is set to several centimeters in view of the cost and easy handlability.

The width 117 of the laser excitation spot is contracted from 100 μm width to 20 μm width to improve the density of laser excitation by 5 times, so that throughput can be improved by 5 times.

An example of this constitution is shown with reference to Examples 7 and 8.

In this example, a constitution of a florescence detection apparatus using a sample flow container and a line sensor is shown in FIG. 18. A light emitted from an Ar$^+$ laser 1 is collected by an achromatic lens 207 to restrict the spot diameter to 25 μm. In this state, a laser light is entered to a sample flow container 105 and propagated in a sample flow channel portion 163 between two quartz substrates 131 and 132. The laser light during propagation excites labeled target molecules 4 in the sample flow channel portion 163 to generate fluorescence. In this case, since a relatively large difference is generally present between the refractive index for the substrate 131, 132 and the refractive index for the sample solution, the light propagates under multiple reflection between the sample solution and the quartz substrates 131, 132. The situation of propagation is identical with that in Example 1 and since the density of the excitation laser intensity can be maximized by setting the thickness of the sample flow channel portion to 25±15 μm as described for Example 1, the thickness for the sample flow channel portion is set to 25 μm also in this example. Further, this can extend the irradiation region up to several millimeters in the laser propagation direction to improve the throughput.

Further, the generated fluorescence is focused by an objective lens 6 having a magnification of 20× and an numerical aperture of 0.75 on a one-dimensional CCD 24. The one-dimensional CCD 24 used has 512 pixels in the laser propagation direction and 10 pixels in the direction perpendicular thereto. Further, the ten pixels are put to binding into one pixel in the CCD (charges for 10 pixels generated by fluorescence are collected into a charge amount for one pixel and transferred by way of a signal line 11 to a data synthesis portion 25), thereby setting the number of pixels of the one-dimensional CCD 24 as 512×1 pixel to output one-dimensional fluorescence images. Labeled target molecules 4 are controlled to a constant flow speed by a liquid control portion 21 constituted with a syringe and a syringe pump, and passed through a sample flow channel portion 163 to reach a liquid waste reservoir 22.

Thus, data synthesis means reconstitute two-dimensional fluorescence images by fine sequentially arranging the fluorescence image data from the one-dimensional CCD 24 with no loss in view of time. The thus obtained two-dimensional fluorescence images are counted for the number of molecules in a target molecule number counting portion 26 and the concentration of target molecules can be measured based on the ratio to the volume of the sample solution passed through the flow container. In this case, counting in the counting portion 26 is conducted as described below. At first, images shown in FIG. 9 are an example of two-dimensional fluorescence images. Since the images are expressed being whitened more as the fluorescence intensity is higher, white dots in the images corresponds to labeled target molecules. Black portions are background with no molecules but also the regions emit a weak light by the irradiation of the laser to the sample solution. Since the intensity is lower compared with the fluorescence intensity from the fluorescence-labeled target molecules, they are expressed black in the images. A target molecule number counting portion evaluates the fluorescence intensity of the background and counts the number of white spots corresponding to the images of fluorescence-labeled target molecules with a difference being larger than a properly determined threshold value, thereby attaining counting for the number of fluorescence-labeled target molecules.

FIG. 19 shows details for the constitution of a sample flow container. For forming a flow channel between two quartz substrates 131 and 132, an indent is formed in the substrate 132 conforming the shape of the sample flow channel portion 163 by dry etching. The thickness of the indent is 25 μm being identical with the thickness of the sample flow channel portion. A spacer 133 between the two quartz substrate in FIG. 19 is formed of a peripheral portion of the substrates 132 being remained after etching.

On the other hand, for forming an inlet 164 and exit 165 to the sample flow channel portion, a through hole is perforated in the upper quartz substrate 131 and then two substrates are bonded. Then, a glass capillary 27 is inserted and bonded to the two through holes, so that the sample solution can be introduced from the syringe of the fluid control portion and discharged to a liquid wastes reservoir.

The width 119 of the sample flow container is set to several mm or more for extending the laser irradiation region. Further, the length 121 of the sample flow container can be decided irrespective of the sample volume to be measured different from the sample container.

With the constitution of the apparatus as described above, a width 117 for the laser excitation spot can be contracted from 100 μm width to 20 μm width and the density of laser excitation can be improved by 5 times, so that the throughput can be improved by 5 times.

Figure 20:
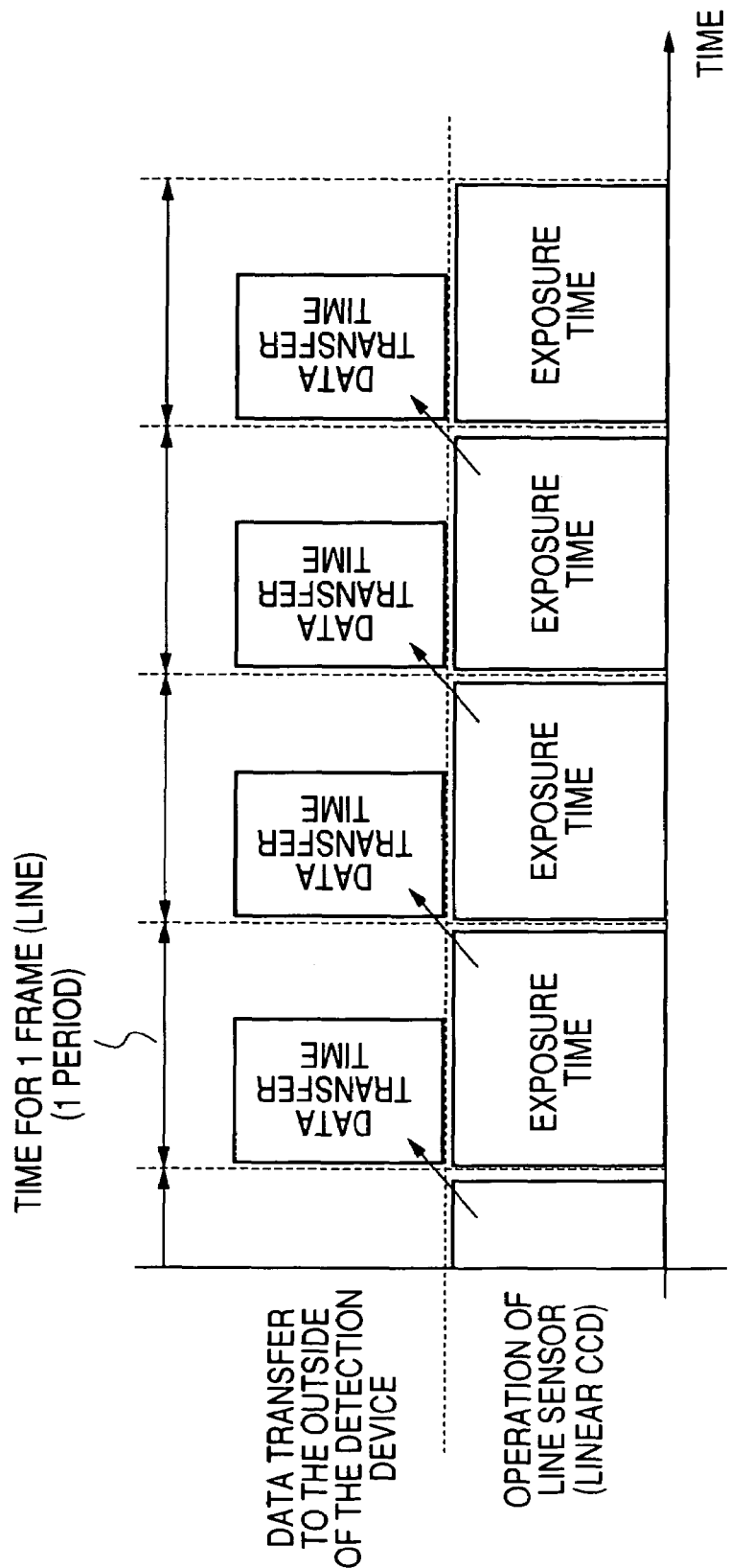
FIG. 20 is a time table for exposure time using the sample flow container and the line sensor in the best embodiment and Example 7 of the invention.

Driving of the one-dimensional CCD 24 is controlled by a trigger signal from a control system. The exposure time is 19.5 msec, the data transfer time is 15 msec, and the processing corresponding to the times is executed simultaneously as shown in FIG. 20. After exposure, data transfer in the one-dimensional CCD 24 is necessary for the preparation of the data transfer, and the time required therefor is 0.5 msec or less. Accordingly, only 2.5% for the entire measuring time is a loss time with no exposure and substantially continuous exposure is attained.

EXAMPLE 8

This example shows a constitution of attaching a film to the substrate of a sample flow container. The constitution other than the film is basically identical with the constitution shown in FIG. 18 and in Example 7. According to the constitution, since the density of laser excitation can be improved for the identical intensity of the laser excitation, the exposure time can be shortened and improvement of the throughput can be expected. Particularly, in the case of a sample flow container, since the ratio of the loss time other than the exposure time during measuring time is small, the throughput can be improved in an inverse proportion with the shortening of the exposure time, and this can improve the effect by the provision of the film to the substrate constituting the sample flow container.

Figure 21:
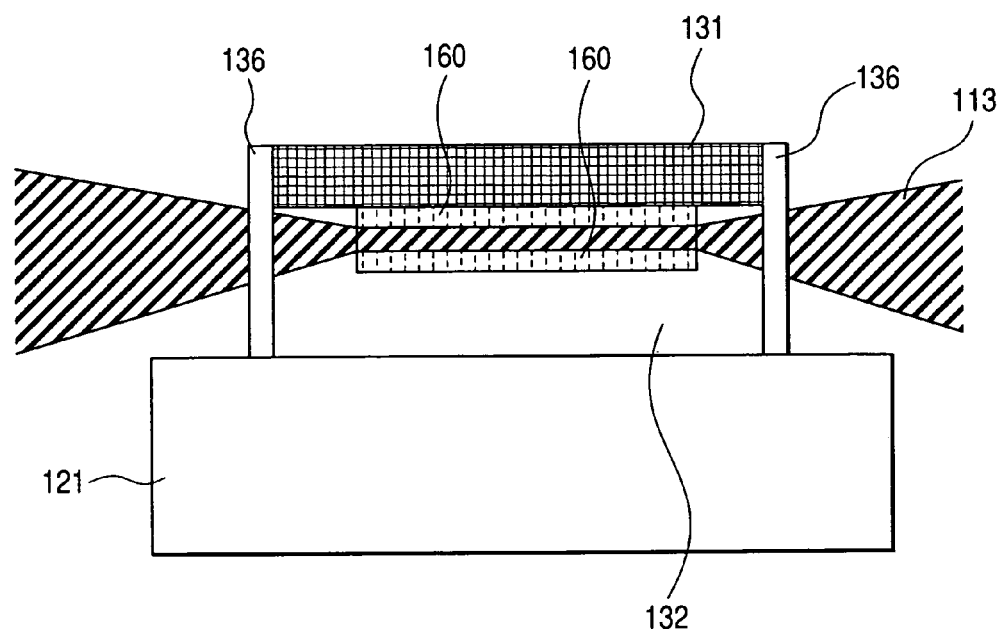
FIG. 21 is a cross sectional view of a sample flow container using a low refractive index thin film in Example 8.

FIG. 21 shows a cross sectional structural view of a sample cell flow container. As shown in FIG. 21, a sample solution (sample) flows between two quartz substrates 131 and 132, and a laser beam 113 collected by an achromatic lens 207 is entered in the solution and excites fluorescence labels during propagation. Since the laser beam can propagate without leaking light in the solution by total reflection at the boundary between the two quartz substrates and the solution, the density of excitation laser intensity can be improved. For attaining the total reflection, it is necessary to form a thin film 160 of refractive index lower than that of the solution is formed to the region of a sample flow channel portion 163. As the material of low refractive index, a fluorocarbon resin is preferred. In this example, an amorphous fluoro polymer (refractive index: 1.29) was used. The range for the refractive index applicable as the material of low refractive index may be smaller by 0.1% than the refractive index of the solution and may be greater than 1.

The upper limit of the refractive index depends on the refractive index of the solution. The refractive index of the solution changes about from 1.33 to 1.37 depending on the concentration of a salt or a polymer other than the fluorescent labeled target molecule. In a case where the refractive index of the solution in the working condition less fluctuates, a film with a refractive index smaller by 0.1% or more than that of the solution to be used is formed and the excitation laser light can be propagated between the two sheets of glass substrates. In a case where the difference of the refractive index is less than 0.1%, it is not practical since the incident condition for the laser is stringent. While a larger difference of the refractive index is preferred since the stability to the change of the refractive index of the solution is higher, since this accompanies light absorption and it is not appropriate for attaining the refractive index of smaller than 1 in the wavelength region used for excitation of phosphor. Actually, a range of refractive index from 1.2 to 1.35 is preferred. The effect of the low refractive index thin film 160 is to be described with reference to FIG. 8. The graph shows mean values for the density of excitation intensity in a case where the laser input intensity to the sample container is made constant at 10 mW relative the thickness of the solution held in the container. The solid line shows a case with no thin film of low refractive index, while the dotted line shows the density of excitation intensity in a case with the thin film with of low refractive index. It is assumed that pure water (refractive index: 1.33) is used for the solution. It can be seen that the density of laser excitation improves more as the thickness of the solution decreases. As the density of laser excitation increases, the detection sensitivity for the fluorescence molecule improves more. Further, decrease of the solution thickness can also relatively decrease the effect of background noises other than the fluorescence (scattering due to the Raman scattering of water or scattering of molecule in the solution). In this example, the thickness of the solution held in the sample container (distance between the first layer and the second layer as the thin film of low refractive index) is set to 15 μm. In a case where the thickness of the sample solution decreases excessively, since the laser irradiation volume is decreased and the throughput is lowered, it is desirable that the thickness is 15 μm or more and it is set to 15 μm. However, since the measuring sensitivity of the target is higher as the thickness is smaller, the thickness is determined also in view of the balance between the throughput and the fluorescence intensity of the fluorescence-label depending on the application use.

Figure 22:
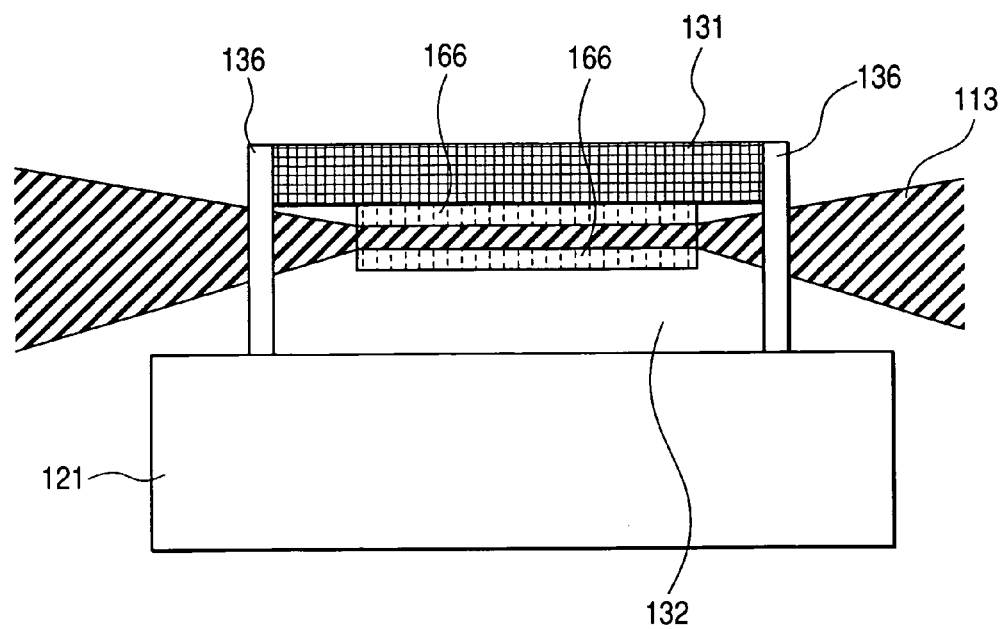
FIG. 22 is a cross sectional view of a sample flow container using a dielectric thin film in Example 8.

Further, it is also effective for the improvement of the density of laser excitation by forming a dielectric film (single or multi-layered dielectric film) instead of the low refractive index film 160 described above, to improve the reflectivity at the boundary between the solution and the glass substrate. FIG. 22 shows a cross sectional view of a sample container using a dielectric (single layer) thin film for the reflection film as a most simple constitution. Instead of the low refractive index thin film (160 in FIG. 21), a dielectric film 166 of higher refractive index than the refractive index of the substrate is formed. That is, a first dielectric film and a second dielectric film are formed each as a thin film on each of the opposing surfaces of the two substrates. With the constitution, total reflection does not occur at the boundary between the dielectric thin film 166 and the solution 167, and a light at a considerably high intensity transmits without reflection. However, since the refractive index of the dielectric thin film 166 is set higher than the refractive index of the glass substrates 131, 132, total reflection occurs at the boundary between the dielectric thin film 166 and the glass substrate (131 or 142). Since the light is reflected with the thickness of the solution 137 being relatively decreased, higher density of excitation laser can be obtained. FIG. 17 shows the density of excitation laser in a case of using SiN (refractive index: 1.95, thickness: 0.4 μm) as the dielectric film by the data depicted with symbol "Δ". As can be seen from FIG. 17, while the excitation density is lower than the case of using the low refractive index thin film, it can be seen that the excitation density improves more than in the case of using only the glass. Since the range of the refractive index of the dielectric thin film has to be higher than the refractive index of the glass as the substrate, it needs a refractive index of 1.45 or more in a case where the index of the glass substrate is 1.45. A favorable intensity of laser excitation can be obtained at the thickness of the sample solution of 15 μm. An optimum range for the thickness of the sample solution is within a range from 10 to 30 μm. Further, it will be apparent that the dielectric film may also be in a multi-layered form. In this case, each of the dielectric films may have a plurality of layers each having different refractive indices and, for example, in a case where each film comprises two layers, the refractive index of the layer in contact with the solution may be higher than that of the layer in contact with the substrate. In a most simple case of the multi-layered structure, an $SiO_2$ layer (refractive index: 1.45) at a thickness of 15 μm as a cladding layer of well controlled refractive index may be inserted between the dielectric film and the substrate. This can obtain more stable total reflection.

Further, as a more complicate case, for example, an SiN layer of 3.6 μm thickness (refractive index: 1.95) is formed at the position 166 on the side of a glass substrate 132, an $SiO_2$ layer of 3.7 μm thickness (refractive index: 1.45) is formed thereon, and the solution is held thereover as shown in FIG. 22. Further, identical two layers are formed being turned upside down on the surface of the upper glass substrate. This can ensure high reflectance of 99% or higher to improve the density of laser excitation. While the example described above shows a reflection film comprising two layers as a multi-layered film, the reflection layer may also be formed by combining more number of layers. The advantage obtained by the use of the dielectric film is to keep the surface in contact with the solution stable and eliminate the possibility of inclusion of unnecessary chemical substances to the sample solution as much as possible. In FIG. 21 and FIG. 22, a glass plate 136 for window is formed to an incident portion of the sample flow container. This is formed by appending a glass plate 136 to an uneven portion of the quartz plates 132, 131 by using an adhesive of an identical refractive index, in order not to cause scattering of light due to the unevenness upon incidence to the sample flow container and reduce the intensity of light in the course of propagation to the solution.

For the constitution of this example, a constitution described in Example 2 can also be applied properly in addition to the constitution described above in this example. This can provide the same effect of reflection as in Example 2 thereby capable of shortening the exposure time and obtain an effect capable of expecting the improvement of the throughput.

Then, the result of conducting the quantitative determination for concentration with the constitution of this example is to be described. A solution in which a double helical DNA of 3.8 kb is labeled with YOYO-1 as an intercalater is used as a sample solution. Three types of solutions at the DNA concentration of $10^{-14}$M, $10^{-13}$M, $10^{-12}$M are provided and the solutions are caused to flow at a constant speed in the sample flow container to measure the number of labeled target molecules. Since the density of the laser intensity can be improved by 5 times by the use of the line sensor in view of the flow speed, the throughput can be improved by 5 times. The reason that the flow speed can be improved by 5 times are to be described below.

Figure 23:
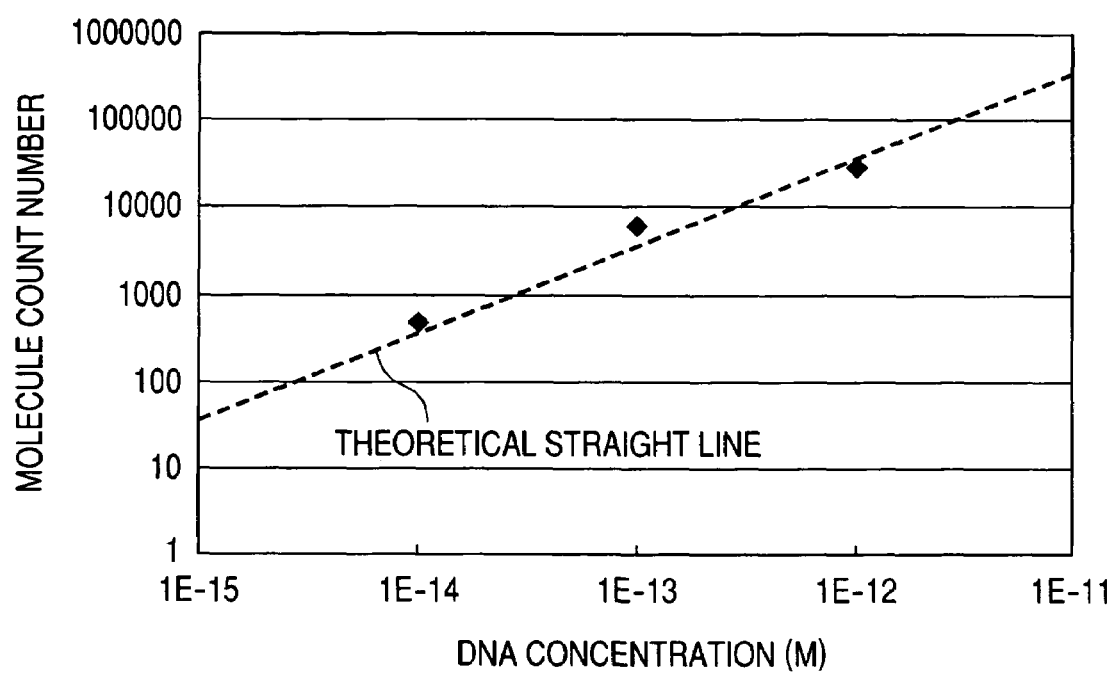
FIG. 23 is a graph showing the result of measurement for a relation between the count for the number of molecules and the concentration.

By increasing the flow speed to 5 times, the size of images of the labeled target molecule on the line sensor is extended by five times at the maximum in the direction parallel with the flow. Accordingly, assuming that the density of the excitation intensity was unchanged, fluctuation of the background corresponding to the fluorescent images (line sensor output in the absence of fluorescence images) is increased to $\sqrt{5}$ times. Since it is assumed that the density of excitation intensity did not change, the fluorescence intensity (signal) does not change and the SN ratio is lowered to $1/\sqrt{5}$ times. However, the density of excitation laser is improved by 5 times by the use of the line sensor. Accordingly, the fluorescence intensity increases by 5 times and the fluctuation of the background increases by $\sqrt{5}$ times. That is, by the use of the line sensor, the density of excitation laser increases by 5 times and the SN ratio increases by $\sqrt{5}$ times. From the foregoings, the lowering amount of the SN ratio when the speed is increased by 5 times is identical with the amount for the improvement of the SN ratio when the density of excitation laser increases by 5 times. Accordingly, even when the flow speed is increased by 5 times by the use of the line sensor, the SN ratio does not change. That is, measurement at a flow speed by five times is possible by the use of the line sensor. FIG. 23 shows the result of actually counting the molecule numbers in the DNA solution at the three kinds of concentrations. The theoretical curve in FIG. 23 shows the number of molecules to be present in the entire measurement volume (0.06 µL) obtained by multiplying 0.01 mL as a volume of an excitation laser irradiation region: 50×10×20 µm, with the number of fluorescence image frames for measuring time of 2 min (60,000). As can be seen from FIG. 23, substantially entire number of molecules can be measured and counted. This shows that the sensitivity is not lowered and the entire molecules can be counted even at the flow speed as high as by five times. It can be demonstrated from FIG. 23 that the constitution of this example can measure the number of molecules of a sample whose concentration is unknown at a throughput of five times, and the concentration can be quantitatively determined based on the value and the measurement volume.

What is claimed is:

1. A fluorescence detection apparatus including a sample holding portion having a first substrate and a second substrate in which a sample solution is held between the first substrate and the second substrate;
    a light irradiation portion for irradiating an excitation light between the first substrate and the second substrate;
    a detection portion for detecting fluorescence caused inside the sample holding portion; and
    transfer means for relatively and mechanically transferring the sample holding portion relative to the detection portion;
    wherein the first substrate and the second substrate each has a first layer and a second layer at surfaces opposed to each other, the first layer and the second layer each having a refractive index higher than that of the sample.

2. A fluorescence detection apparatus according to claim 1, wherein the first substrate and the second substrate each has a first dielectric film and a second dielectric film at surfaces opposed to each other, and the first dielectric film and the second dielectric film each has a refractive index higher than that of the first substrate and the second substrate.

3. A fluorescence detection apparatus according to claim 2, wherein the first dielectric film and the second dielectric film each has a plurality of layers of different refractive indices.

4. A fluorescence detection apparatus according to claims 1 or 2, wherein the first substrate and the second substrate are disposed horizontally.

5. A fluorescence detection apparatus according to claim 1, wherein the first substrate and the second substrate are substantially parallel.

6. A fluorescence detection apparatus according to claim 1, wherein the distance between the first substrate and the second substrate is not less than 10 µm and not greater than 40 µm.

7. A fluorescence detection apparatus according to claim 1, wherein the distance between the first substrate and the second substrate is 15 µm or more.

8. A fluorescence detection apparatus according to claim 1, wherein the first layer and the second layer each comprise a fluorocarbon resin.

9. A fluorescence detection apparatus according to claims 1 or 2, wherein a spacer means is provided between first substrate and the second substrate.

10. A fluorescence detection apparatus according to claim 1, wherein the light irradiation portion irradiates the excitation light in a direction parallel to the first substrate and the second substrate.

11. A fluorescence detection apparatus according to claim 1, wherein the apparatus further includes a cover portion in contact with at least a portion of the sample holding portion along the incident direction of the excitation light.

12. A fluorescence detection apparatus according to claims 1 or 2, wherein the sample holding portion further has a sample introduction port and a sample delivery portion.

13. A fluorescence detection apparatus according to claims 1 or 2, wherein the light irradiation portion controls the excitation light such that the diameter in the horizontal direction of the excitation light is larger than the diameter in the direction perpendicular to the excitation light at the central portion of the sample holding portion.

14. A fluorescence detection apparatus according to claim 1, wherein the apparatus has a light detector for detecting the intensity of the excitation light passing through the sample holding portion and a control portion for receiving the output of the light detector, wherein the control portion controls the transfer means to effect transfer of the sample holding portion in a vertical direction according to the output of the light detector.

15. A fluorescence detection apparatus according to claim 1, wherein the detection portion has a first lens having a magnification of M1 and a numerical aperture of NA1 and a second lens having a numerical aperture of NA2, and a light detection device, in which the first lens is disposed at a position nearer to the sample holding portion than the second lens, and the first lens and the second lens satisfy a relation: NA2>NA1×M1.

16. A fluorescence detection apparatus according to claims 1 or 2, wherein the first lens is disposed on the first substrate and the second lens is a concave/convex portion formed on the first substrate.

17. A method of detecting fluorescence including the steps of:
- introducing a sample to a sample holding portion having a first substrate and a second substrate;
- irradiating an excitation light between the first substrate and the second substrate, and
- moving the sample holding portion to a detection portion and detecting fluorescence generated inside the sample holding portion;
- wherein the sample is moved by a pressure difference between a sample introduction port and a sample delivery port.

18. A method of detecting fluorescence including the steps of:
- introducing a sample to a sample holding portion having a first substrate and a second substrate;
- irradiating an excitation light between the first substrate and the second substrate, and
- moving the sample holding portion to a detection portion and detecting fluorescence generated inside the sample holding portion;
- wherein a period for moving the sample holding portion to the detection portion and a period for outputting the detection data from the detection portion are overlapped.

19. A fluorescence detection apparatus including a sample holding portion having a first substrate and a second substrate, wherein a sample solution is held between the first substrate and the second substrate,
- a liquid control portion for controlling a flow of the sample solution in the sample holding portion,
- a light irradiation portion for irradiating an excitation light between the first substrate and the second substrate, and
- a sensor disposed in one-dimensional form for detecting fluorescence generated inside the sample holding portion.

20. A fluorescence detection apparatus according to claim 19, wherein the sensor is disposed substantially parallel with an irradiation direction of the excitation light.

21. A fluorescence detection apparatus according to claim 19, wherein the liquid control portion controls the flow of the sample solution in the sample holding portion at a constant flow rate.

22. A fluorescence detection apparatus according to claim 19, wherein the apparatus further includes data synthesizing means for synthesizing data of distribution a of two-dimensional intensity of fluorescence by using data detected by the sensor.

23. A fluorescence detection apparatus according to claim 22, wherein the apparatus further includes counting means for counting the number of target molecules in the sample solution by using the data of the distribution of two-dimensional intensity of fluorescence synthesized by the data synthesizing means.

24. A fluorescence detection apparatus according to claim 19, wherein the first substrate and the second substrate each has a first layer and a second layer at the surfaces opposed to each other, and the first layer and the second layer each has a refractive index lower than that of the sample solution.

25. A fluorescence detection apparatus according to claim 24, wherein the distance between the first layer and the second layer is 15 μm or more.

26. A fluorescence detection apparatus according to claim 19, wherein the first substrate and the second substrate each has a first dielectric film and a second dielectric film at the surfaces opposed to each other, and the first dielectric film and the second dielectric film each has a refractive index lower than that of the first substrate and the second substrate.

27. A fluorescence detection apparatus according to claim 19, wherein the distance between the first substrate and the second substrate is not less than 10 μm and not greater than 40 μm.

28. A fluorescence detection apparatus according to claim 19, wherein the light irradiation portion irradiates the excitation light in a direction substantially parallel with the first substrate and the second substrate and substantially perpendicular to the direction of the flow of the sample solution.

* * * * *